US009198424B2

(12) United States Patent
Funke et al.

(10) Patent No.: US 9,198,424 B2

(45) Date of Patent: Dec. 1, 2015

(54) ACTIVE INGREDIENT COMBINATIONS HAVING INSECTICIDAL AND ACARICIDAL PROPERTIES

(75) Inventors: Christian Funke, Leichlingen (DE); Heike Hungenberg, Langenfeld (DE); Rüdiger Fischer, Pulheim (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 141 days.

(21) Appl. No.: 13/161,960

(22) Filed: Jun. 16, 2011

(65) Prior Publication Data

US 2011/0311503 A1 Dec. 22, 2011

Related U.S. Application Data

(60) Provisional application No. 61/356,224, filed on Jun. 18, 2010.

(30) Foreign Application Priority Data

Jun. 18, 2010 (EP) .................................... 10166439

(51) Int. Cl.

| | |
|---|---|
| ***A01N 43/713*** | (2006.01) |
| ***A01N 43/08*** | (2006.01) |
| ***A01N 43/56*** | (2006.01) |
| ***A61K 31/4439*** | (2006.01) |
| ***A61K 31/661*** | (2006.01) |
| ***A61K 31/70*** | (2006.01) |
| *A61K 45/06* | (2006.01) |

(52) U.S. Cl.

CPC .............. *A01N 43/713* (2013.01); *A01N 43/08* (2013.01); *A01N 43/56* (2013.01); *A61K 31/4439* (2013.01); *A61K 31/661* (2013.01); *A61K 31/70* (2013.01); *A61K 45/06* (2013.01)

(58) Field of Classification Search

None

See application file for complete search history.

(56) References Cited

U.S. PATENT DOCUMENTS

| | | | |
|---|---|---|---|
| 2004/0116744 | A1 | 6/2004 | Furuya et al. |
| 2007/0066617 | A1 | 3/2007 | Mita et al. |
| 2007/0129407 | A1 | 6/2007 | Koyanagi et al. |
| 2007/0142327 | A1 | 6/2007 | Funke et al. |
| 2008/0070863 | A1 | 3/2008 | Funke et al. |
| 2008/0305955 | A1 | 12/2008 | Bretschneider et al. |
| 2009/0076282 | A1 | 3/2009 | Toriyabe et al. |
| 2009/0111847 | A1 | 4/2009 | Li et al. |
| 2009/0247551 | A1 | 10/2009 | Jeschke et al. |
| 2009/0253749 | A1 | 10/2009 | Jeschke et al. |
| 2009/0259046 | A1 | 10/2009 | Hamamoto et al. |
| 2010/0029478 | A1 | 2/2010 | Alig et al. |
| 2010/0240705 | A1 | 9/2010 | Jeschke et al. |
| 2010/0292226 | A1 | 11/2010 | Funke et al. |
| 2011/0195998 | A1 | 8/2011 | Goto et al. |
| 2011/0212949 | A1 | 9/2011 | Bretschneider et al. |
| 2011/0257191 | A1 | 10/2011 | Fischer et al. |
| 2011/0306499 | A1 | 12/2011 | Bretschneider et al. |

FOREIGN PATENT DOCUMENTS

| | | |
|---|---|---|
| EP | 0 539 588 | 5/1993 |
| JP | 2008-110953 | 5/2008 |
| JP | 2010-018586 | 1/2010 |
| WO | 02/096882 | 12/2002 |
| WO | 03/106457 | 12/2003 |
| WO | 2004/046129 | 6/2004 |
| WO | 2005/035486 | 4/2005 |
| WO | 2005/048713 | 6/2005 |
| WO | 2005/053393 | 6/2005 |
| WO | 2005/053406 | 6/2005 |
| WO | 2005/063094 | 7/2005 |
| WO | 2005/077934 | 8/2005 |
| WO | 2005/085216 | 9/2005 |
| WO | 2006/043635 | 4/2006 |
| WO | 2006/056433 | 6/2006 |
| WO | 2006/089633 | 8/2006 |
| WO | 2006/100288 | 9/2006 |
| WO | 2007/017433 | 2/2007 |
| WO | 2007/040280 | 4/2007 |
| WO | 2007/057407 | 5/2007 |
| WO | 2007/075459 | 7/2007 |
| WO | 2007/101369 | 9/2007 |
| WO | 2007/115643 | 10/2007 |
| WO | 2007/115644 | 10/2007 |
| WO | 2007/115646 | 10/2007 |
| WO | 2007/144100 | 12/2007 |
| WO | 2007/149134 | 12/2007 |
| WO | 2008/066153 | 6/2008 |
| WO | 2008/067911 | 6/2008 |
| WO | 2008/072783 | 6/2008 |
| WO | 2008/104503 | 9/2008 |
| WO | 2009/049851 | 4/2009 |
| WO | 2010/005692 | 1/2010 |
| WO | 2010/006713 | 1/2010 |
| WO | 2010/074747 | 7/2010 |
| WO | 2010/074751 | 7/2010 |
| WO | 2011/098408 | 8/2011 |

OTHER PUBLICATIONS

International Search Report Based on Application No. PCT/EP2011/059988 Dated Nov. 30, 2011.

Colby; "Calculating Synergistic and Antagonistic Responses of Herbicide Combinations"; Weeds; 1967; vol. 15; pp. 20-22.

*Primary Examiner* — Bethany Barham

*Assistant Examiner* — Barbara Frazier

(74) *Attorney, Agent, or Firm* — Miles & Stockbridge P.C.

(57) ABSTRACT

The novel active ingredient combinations which consist of the compounds of the formula (I) in combination with further active insecticidal ingredients (II) are very suitable for control of animal pests such as insects and/or unwanted acarids.

12 Claims, No Drawings

ACTIVE INGREDIENT COMBINATIONS HAVING INSECTICIDAL AND ACARICIDAL PROPERTIES

CROSS REFERENCE TO RELATED APPLICATIONS

This application claims priority to EP 10166439.9 filed Jun. 18, 2010 and U.S. 61/356,224 filed Jun. 18, 2010, the contents of which are both incorporated herein by reference in their entireties.

BACKGROUND

1. Field of the Invention

The present invention relates to novel active ingredient combinations which consist of the compounds of the formula (I) in combination with further active insecticidal ingredients (II) and are very suitable for control of animal pests such as insects and/or unwanted acarids.

2. Description of Related Art

Some of the compounds of the formula (I) are known from WO 2007/144100 and their insecticidal action has been described. The active ingredients specified in this description by their common name are known, for example, from "The Pesticide Manual" 14th ed., British Crop Protection Council 2006, and the website http://www.alanwood.net/pesticides.

However, the acaricidal and/or insecticidal efficacy and/or the activity spectrum and/or the compatibility of the known compounds with plants, especially with respect to crop plants, is not always adequate.

SUMMARY

It has now been found that active ingredient combinations comprising the compounds of the general formula (I)

(I)

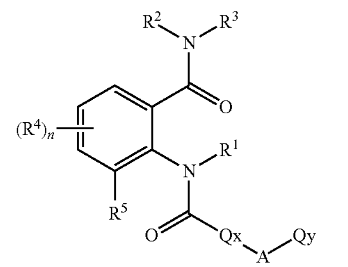

in which $R^1$ is hydrogen, amino, hydroxyl or in each case optionally $C_1$-$C_6$-alkyl, $C_2$-$C_6$-alkenyl, $C_2$-$C_6$-alkynyl or $C_3$-$C_6$-cycloalkyl, where the substituents may each independently be selected from halogen, cyano, nitro, hydroxyl, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)carbonyl, $C_1$-$C_4$-alkylamino, di-($C_1$-$C_4$-alkyl)amino, $C_3$-$C_6$-cycloalkylamino or ($C_1$-$C_4$-alkyl)$C_3$-$C_6$-cycloalkylamino, $R^2$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkylamino, di-($C_1$-$C_4$-alkyl)amino, $C_3$-$C_6$-cycloalkylamino, $C_1$-$C_6$-alkoxycarbonyl or $C_1$-$C_6$-alkylcarbonyl, $R^3$ is hydrogen or in each case optionally mono- or polysubstituted identically or differently, $C_1$-$C_6$-alkyl, $C_1$-$C_6$-alkoxy, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl, where the substituents may each independently be selected from amino, $C_3$-$C_6$-cycloalkylamino, halogen, cyano, carboxyl, carbamoyl, nitro, hydroxyl, $C_1$-$C_6$-alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_6$-alkoxycarbonyl, $C_1$-$C_6$-alkylcarbonyl, $C_3$-$C_6$-trialkylsilyl or a saturated or partly saturated heterocyclic ring, an aromatic or heteroaromatic ring or a saturated, partly saturated or aromatic heterobicyclic ring, where the ring or ring system is optionally mono- or polysubstituted identically or differently by $SF_5$, halogen, cyano, nitro, hydroxyl, amino, carboxyl, carbamoyl, aminosulphonyl, $C_1$-$C_6$-alkyl, $C_3$-$C_6$-cycloalkyl, $C_1$-$C_4$-alkoxy, $C_1$-$C_6$-haloalkyl, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_1$-$C_6$-alkoxycarbonyl, $C_1$-$C_6$-alkylcarbonyl, $C_3$-$C_6$-trialkylsilyl, benzyl $C_2$-$C_6$-alkenyl, $C_2$-$C_6$-alkynyl, $C_2$-$C_6$-haloalkenyl, $C_2$-$C_6$-haloalkynyl, $C_3$-$C_6$-halocycloalkyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, or a 3- to 6-membered ring, where the ring may optionally be substituted by $C_1$-$C_6$-alkyl, halogen, cyano, nitro, halo($C_1$-$C_6$)-alkyl, $C_1$-$C_6$-alkoxy or halo($C_1$-$C_6$)-alkoxy, or $R^3$ is $C_1$-$C_6$-alkoxycarbonyl, $C_1$-$C_6$-alkylcarbonyl, $C_1$-$C_6$-alkylaminocarbonyl or di($C_1$-$C_6$)alkylaminocarbonyl, or $R^3$ is additionally a mono- or polysubstituted identically or differently, 5- or 6-membered aromatic or heteroaromatic ring, a 4, 5- or 6-membered partly saturated ring or saturated heterocyclic ring, or a saturated, partly saturated or aromatic heterobicyclic ring which may optionally contain one to three heteroatoms from the group of O, S and N, where the substituents are each independently selected from $SF_5$, halogen, cyano, nitro, hydroxyl, amino, carboxyl, carbamoyl, $C_1$-$C_6$-alkyl, $C_3$-$C_6$-cycloalkyl, $C_1$-$C_4$-alkoxy, $C_1$-$C_6$-haloalkyl, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_1$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_1$-$C_6$-alkoxycarbonyl, $C_1$-$C_6$-alkylcarbonyl, $C_3$-$C_6$-trialkylsilyl, $C_2$-$C_6$-alkenyl, $C_2$-$C_6$-alkynyl, $C_2$-$C_6$-haloalkenyl, $C_2$-$C_6$-haloalkynyl, $C_3$-$C_6$-halocycloalkyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, or a 3- to 6-membered ring, where the ring may optionally be substituted by $C_1$-$C_6$-alkyl, halogen, cyano, nitro, halo($C_1$-$C_6$)-alkyl, $C_1$-$C_6$-alkoxy or halo($C_1$-$C_6$)-alkoxy, $R^2$ and $R^3$ may be joined to one another via two to six carbon atoms and form a ring which optionally additionally contains a further nitrogen, sulphur or oxygen atom and may optionally be mono- to tetrasubstituted by $C_1$-$C_2$-alkyl, $C_1$-$C_2$-haloalkyl, halogen, cyano, amino $C_1$-$C_2$-alkoxy or $C_1$-$C_2$-haloalkoxy, $R^2$, $R^3$ together are additionally $=S(C_1$-$C_4$-alkyl$)_2$, $=S(O)(C_1$-$C_4$-alkyl$)_2$, $R^4$ is hydrogen, halogen, cyano, nitro $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$- haloalkylsulphonyl, $C_1$-$C_4$-alkylamino, di-($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, or two $R^4$ via adjacent carbon atoms form a ring which is —$(CH_2)_3$—, —$(CH_2)_4$—, —$(CH_2)_5$—, —(CH═CH—$)_2$—, —$OCH_2O$—, —$O(CH_2)_2O$—, —$OCF_2O$—, —$(CF_2)_2O$—, —$O(CF_2)_2O$—, —(CH═CH—CH═N)— or —(CH═CH—N═CH)—, two $R^4$ via adjacent carbon atoms additionally form the following fused rings which are optionally mono- or polysubstituted identically or differently, where the substituents may each independently be selected from hydrogen, $C_1$-$C_6$-alkyl, $C_3$-$C_6$-cycloalkyl, $C_1$-$C_6$-haloalkyl, $C_3$-$C_6$-halocycloalkyl, halogen, $C_1$-$C_6$-alkoxy, $C_1$-$C_4$-alkylthio($C_1$-$C_6$-alkyl), $C_1$-$C_4$-alkylsulphinyl($C_1$-$C_6$-alkyl), $C_1$-$C_4$-alkylsulphonyl($C_1$-$C_6$-alkyl), $C_1$-$C_4$-alkylamino, di-($C_1$-$C_4$-alkyl)amino or $C_3$-$C_6$-cycloalkylamino,

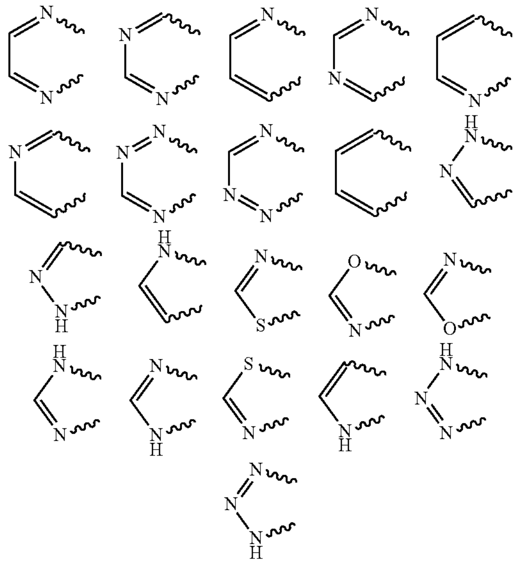

n is 0 to 3, $R^5$ is $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $Q_X$ is an optionally singly or multiply, identically or differently $R^7$-substituted, aromatic or heteroaromatic 5- to 6-membered ring which may contain 1-3 heteroatoms from the group of N, S, O, A is optionally mono- or polysubstituted —($C_1$-$C_6$-alkylene)-, —($C_2$-$C_6$-alkenylene)-, —($C_2$-$C_6$-alkynylene)-, —$R^8$—($C_3$-$C_6$-cycloalkyl)-$R^8$—, —$R^8$—O—$R^8$—, —$R^8$—S—$R^8$—, —$R^8$—S(═O)—$R^8$—, —$R^8$—S(═O$)_2$—$R^8$—, —$R^8$—N($C_1$-$C_6$-alkyl)-$R^8$—, —$R^8$—C═NO($C_1$-$C_6$-alkyl)-$R^8$, —CH[$CO_2$($C_1$-$C_6$-alkyl)-, —$R^8$—C(═O)—$R^8$, —$R^8$—C(═O)NH—$R^8$, $R^8$—C(═O)N($C_1$-$C_6$-alkyl)-$R^8$, —$R^8$—C(═O)NHNH—$R^8$—, —$R^8$—C(═O)N($C_1$-$C_6$-alkyl)-NH—$R^8$—, —$R^8$—C(═O)NHN($C_1$-$C_6$-alkyl)-$R^8$, —$R^8$—O(C═O)—$R^8$, —$R^8$—O(C═O)NH—$R^8$, —$R^8$—O(C═O)N($C_1$-$C_6$-alkyl)-$R^8$, —$R^8$—S(═O$)_2$NH—$R^8$, —$R^8$—S(═O$)_2$N($C_1$-$C_6$-alkyl)-$R^8$, —$R^8$—S(C═O)—$R^8$, —$R^8$—S(C═O)NH—$R^8$, —$R^8$—S(C═O)N($C_1$-$C_6$-alkyl)-$R^8$, —$R^8$—NHNH—$R^8$, —$R^8$—NHN($C_1$-$C_6$-alkyl)-$R^8$, —$R^8$—N($C_1$-$C_6$-alkyl)-NH—$R^8$, —$R^8$—N($C_1$-$C_6$-alkyl)-N($C_1$-$C_6$-alkyl)-$R^8$, —$R^8$—N═CH—O—$R^8$, —$R^8$—NH(C═O)O—$R^8$, —$R^8$—N($C_1$-$C_6$-alkyl)-(C═O)O—$R^8$, —$R^8$—NH(C═O)NH—$R^8$, —$R^8$—NH(C═S)NH—$R^8$, —$R^8$—NHS(═O$)_2$—$R^8$, $R^8$—NH—$R^8$, $R^8$—C(═O)—C(═O)—$R^8$, $R^8$—C(OH)—$R^8$, $R^8$—NH(C═O)—$R^8$, $R^8$-$Q_Z$-$R^8$, $R^8$—C(═N—NR'$_2$)—$R^8$, $R^8$—C(═C—R'$_2$)—$R^8$ or —$R^8$—N($C_1$-$C_6$-alkyl)S(═O$)_2$—$R^8$, where the substituents may each independently be selected from halogen, cyano, nitro, hydroxyl, C1-C6-alkyl, C1-C6-alkoxy, halogen-C1-C6-alkyl, amino, (C1-C6-alkyl)amino, di(C1-C6-alkyl)amino, C3-C6-cycloalkyl where —(C3-C6-cycloalkyl)- in the ring may optionally contain 1 to 2 heteroatoms selected from the group of N, S, O, $R^8$ is linear or branched —($C_1$-$C_6$-alkylene)- or a direct bond, where two or more $R^8$ are independently linear or branched-($C_1$-$C_6$-alkylene)- or a direct bond, for example $R^8$—O—$R^8$— is —($C_1$-$C_6$-alkylene)-O—($C_1$-$C_6$-alkylene)-, —($C_1$-$C_6$-alkylene)-O—, —O—($C_1$-$C_6$-alkylene)-, or —O—, where R' is alkyl, alkylcarbonyl, alkenyl, alkynyl, which may optionally be mono- or poly-halogen-substituted, $Q_Z$ is a 3- to 4-membered, partly saturated or saturated, or a 5- to 6-membered, partly saturated, saturated or aromatic ring or a 6- to 10-membered bicyclic ring system, where the ring or bicyclic ring system may optionally contain 1-3 heteroatoms from the group of N, S, O, where the ring or bicyclic ring system is optionally mono- or polysubstituted identically or differently, and where the substituents may each independently be selected from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, carbamoyl, nitro, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, $Q_Y$ is a 5- or 6-membered, partly saturated or saturated heterocyclic or heteroaromatic ring or an aromatic 8-, 9- or 10-membered fused heterobicyclic ring system, where the ring or ring system is optionally mono- or polysubstituted, identically or differently, and where the substituents may each independently be selected from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, carboxyl, carbamoyl, nitro, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)alkylsilyl, ($C_1$-$C_4$-alkyl)($C_1$-$C_4$-alkoxy)imino, or where the substituents may each independently be selected from phenyl or a 5- or 6-membered heteroaromatic ring, where phenyl or the ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, nitro, hydroxyl, $C_1$-$C_4$-alkoxy, $C_1$-$C_4$-haloalkoxy, $R^7$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_3$-$C_6$-cycloalkoxy or

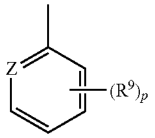

$R^9$ is independently hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, p is 0 to 4, Z is N, CH, CF, CCl, CBr or CI, the compounds of the general formula (I) also including N-oxides and salts (I), and one or more further insecticides and/or acaricides from the group (II):

(1) Acetylcholinesterase (AChE) inhibitors, for example carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example organochlorines, for example chlordane and endosulfan (alpha-); or fiproles (phenylpyrazoles), for example ethiprole, fipronil, pyrafluprole and pyriprole.

(3) Sodium channel modulators/voltage-dependent sodium channel blockers, for example pyrethroids, for example acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; or DDT; or methoxychlor.

(4) Nicotinergic acetylcholine receptor agonists, for example neonicotinoids, for example acetamiprid, clothianidin, dinotefuran, imidacloprid, nitenpyram, thiacloprid, thiamethoxam; or nicotine.

(5) Allosteric acetylcholine receptor modulators (agonists), for example spinosyns, for example spinetoram and spinosad.

(6) chloride channel activators, for example avermectins/milbemycins, for example abamectin, emamectin benzoate, lepimectin and milbemectin.

(7) Juvenile hormone analogues, for example hydroprene, kinoprene, methoprene; or fenoxycarb; pyriproxyfen.

(8) Active ingredients with unknown or nonspecific mechanisms of action, for example fumigants, for example methyl bromide and other alkyl halides; or chloropicrin; sulphuryl fluoride; borax; tartar emetic.

(9) Selective antifeedants, for example pymetrozine; or flonicamid.

(10) mite growth inhibitors, for example clofentezine, diflovidazin, hexythiazox, etoxazole.

(11) microbial disruptors of the insect gut membrane, for example *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT plant proteins, for example Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron; or organotin compounds, for example azocyclotin, cyhexatin, fenbutatin oxide; or propargite; tetradifon.

(13) Oxidative phosphorylation decouplers acting by interrupting the H proton gradient, for example chlorfenapyr and DNOC.

(14) Nicotinergic acetylcholine receptor antagonists, for example bensultap, cartap (hydrochloride), thiocylam, and thiosultap (sodium).

(15) Chitin biosynthesis inhibitors, type 0, for example benzoylureas, for example bistrifluoron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting disruptors, for example cyromazine.

(18) Ecdysone agonists/disruptors, for example diacylhydrazines, for example chromafenozide, halofenozide, methoxyfenozide and tebufenozide.

(19) Octopaminergic agonists, for example amitraz.

(20) Complex-III electron transport inhibitors, for example hydramethylnone; acequinocyl; fluacrypyrim.

(21) Complex-I electron transport inhibitors, for example from the group of the METI acaricides, for example fenazaquin, fenpyroximate, pyrimidifen, pyridaben, tebufenpyrad, tolfenpyrad; or rotenone (Denis).

(22) Voltage-dependent sodium channel blockers, for example indoxacarb; metaflumizone.

(23) Inhibitors of acetyl-CoA carboxylase, for example tetronic acid derivatives, for example spirodiclofen and spiromesifen; or tetramic acid derivatives, for example spirotetramat.

(24) Complex-IV electron transport inhibitors, for example phosphines, for example aluminium phosphide, calcium phosphide, phosphine, zinc phosphide; or cyanide.

(25) Complex-II electron transport inhibitors, for example cyenopyrafen.

(28) Ryanodine receptor effectors, for example diamides, for example chlorantraniliprole and flubendiamide.

Further active ingredients with unknown mechanism of action, for example amidoflumet, azadirachtin, benclothiaz, benzoximate, bifenazate, bromopropylate, chinomethionat, cryolite, cyantraniliprole (Cyazypyr), cyflumetofen, dicofol, diflovidazin, fluensulfone, flufenerim, flufiprole, fluopyram, fufenozide, imidaclothiz, imicyafos, iprodione, pyridalyl, pyrifluquinazon and iodomethane; and also preparations based on *Bacillus firmus* (1-1582, BioNeem, Votivo), further compounds such as dichloropropene, oil (for example petroleum), metaldehyde, metam-sodium, and the following known active compounds:

3-bromo-N-{2-bromo-4-chloro-6-[(1-cyclopropylethyl) carbamoyl]phenyl}-1-(3-chloropyridin-2-yl)-1H-pyrazole-5-carboxamide (known from WO2005/077934), 4-{[(6-bromopyrid-3-yl)methyl](2-fluoroethyl)amino}furan-2(5H)-one (known from WO2007/115644), 4-{[(6-fluoropyrid-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chloropyrid-3-yl)methyl](2-fluoroethyl)amino}furan-2(5H)-one (known from WO2007/115644), 4-{[(6-chloropyrid-3-yl)methyl](2,2-difluoroethyl)amino}furan-2(5H)-one (known from WO2007/115644), 4-{[(6-chloro-5-fluoropyrid-3-yl)methyl](methyl) amino}furan-2(5H)-one (known from WO2007/115643), 4-{[(5,6-dichloropyrid-3-yl)methyl](2-fluoroethyl) amino}furan-2(5H)-one (known from WO2007/115646), 4-{[(6-chloro-5-fluoropyrid-3-yl)methyl](cyclopropyl) amino}furan-2(5H)-one (known from WO2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), {[1-(6-chloropyridin-3-yl)ethyl](methyl) oxido-$\lambda^4$-sulphanylidene}cyanamide (known from WO2007/149134) and its diastereomers {[(1R)-1-(6-chloropyridin-3-yl)ethyl](methyl)oxido-$\lambda^4$-sulphanylidene}cyanamide (A) and {[(1S)-1-(6-chloropyridin-3-yl)ethyl](methyl)oxido-$\lambda^4$-sulphanylidene}cyanamide (B) (likewise known from WO2007/149134) and sulfoxaflor (likewise known from WO2007/149134) and its diastereomers [(R)-methyl(oxido){(1R)-1-[6-(trifluoromethyl)pyridin-3-yl]ethyl}-$\lambda^4$-sulphanylidene]cyanamide (A1) and [(S)-methyl(oxido){(1S)-1-[6-(trifluoromethyl)pyridin-3-yl]ethyl}-$\lambda^4$-sulphanylidene] cyanamide (A2), designated as diastereomer group A (known from WO 2010/074747, WO 2010/074751), [(R)-methyl (oxido){(1S)-1-[6-(trifluoromethyl)pyridin-3-yl]ethyl}-$\lambda^4$-sulphanylidene]cyanamide (B1) and [(S)-methyl(oxido) {(1R)-1-[6-(trifluoromethyl)pyridin-3-yl]ethyl}-$\lambda^4$-sulphanylidene]cyanamide (B2), designated as diastereomer group B (likewise known from WO 2010/074747, WO 2010/074751), and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5] dec-3-en-2-one (known from WO2008/067911), 1-{2-fluoro-4-methyl-5-[(2,2,2-trifluoroethyl)sulphinyl]phenyl}-3-(trifluoromethyl)-1H-1,2,4-triazol-5-amine (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO2008/066153), 2-cyano-3-(difluoromethoxy)-N,N-dimethylbenzenesulphonamide (known from WO2006/056433), 2-cyano-3-(difluoromethoxy)-N-methylbenzenesulphonamide (known from WO2006/100288), 2-cyano-3-(difluoromethoxy)-N-ethylbenzenesulphonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazol-2-amine (known from WO2008/104503), {1'-[(2E)-3-(4-chlorophenyl)prop-2-en-1-yl]-5-fluorospiro [indole-3,4'-piperidin]-1(2H)-yl}(2-chloropyridin-4-yl) methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), 2-ethyl-7-methoxy-3-methyl-6-[(2,2,3,3-tetrafluoro-2,3-dihydro-1,4-benzodioxin-6-yl)oxy]quinolin-4-yl methyl carbonate (known from JP2008/110953), 2-ethyl-7-methoxy-3-methyl-6-[(2,2,3,3-tetrafluoro-2,3-dihydro-1,4-benzodioxin-6-yl)oxy]quinolin-4-yl acetate (known from JP2008/110953), PF1364 (CAS Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl) amino}-1,3-oxazol-2(5H)-one, 4-{[(6-chloropyridin-3-yl) methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl) amino}-1,3-oxazol-2(5H)-one (all known from WO2010/005692), NNI-0711 (known from WO2002096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002096882), methyl 2-[2-({[3-bromo-1-(3-chloropyridin-2-yl)-1H-pyrazol-5-yl] carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl] carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl] carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2- ethylhydrazinecarboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713)

are very suitable for control of animal pests such as insects and/or acaricides. The active ingredients of group (II) are, in accordance with the IRAC classification, assigned to different classes and groups according to their mechanism of action.

DETAILED DESCRIPTION OF A PREFERRED EMBODIMENT

If, within this description, the short form of the common name of an active ingredient is used, this in each case encompasses all common derivatives, such as the esters and salts, and isomers, especially optical isomers, especially the commercial form or forms. If an ester or salt is referred to by the common name, this also refers in each case to all other common derivatives, such as other esters and salts, the free acids and neutral compounds, and isomers, especially optical isomers, especially the commercial form or forms. The chemical compound names mentioned refer to at least one of the compounds encompassed by the common name, frequently a preferred compound.

Surprisingly, the insecticidal and/or acaricidal action of the inventive active ingredient combinations is much higher than the total of the actions of the individual active ingredients. There is an unforeseeable true synergistic effect and not just complementary action.

Preferred combinations comprise at least one of the active ingredients of the formula (I) specified as preferred, more preferred, even more preferred or especially preferred and one or more active ingredients selected from the group (II). Preferred, more preferred, even more preferred or especially preferred are active ingredients of the formula (I) where $R^1$ is preferably hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulphinyl-$C_1$-$C_4$-alkyl or $C_1$-$C_4$-alkylsulphonyl-$C_1$-$C_4$-alkyl, $R^1$ is more preferably hydrogen, methyl, ethyl, cyclopropyl, cyanomethyl, methoxymethyl, methylthiomethyl, methylsulphinylmethyl or methylsulphonylmethyl, $R^1$ is even more preferably hydrogen, $R^2$ is preferably hydrogen or $C_1$-$C_6$-alkyl.

$R^2$ is more preferably hydrogen or methyl.

$R^2$ is even more preferably hydrogen.

$R^3$ is preferably hydrogen or in each case optionally mono- or polysubstituted identically or differently, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl, where the substituents may each independently be selected from halogen, cyano, carboxyl, carbamoyl, nitro, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkoxycarbonyl, $C_1$-$C_4$-alkylcarbonyl or a phenyl ring or a 4, 5- or 6-membered, aromatic partly saturated or saturated heterocyclic ring, where the phenyl ring or heterocyclic ring is optionally mono- or polysubstituted identically or differently, and where the substituents may each independently be selected from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, carboxyl, carbamoyl, $NO_2$, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl or $R^3$ is preferably $C_2$-$C_4$-alkoxycarbonyl, $C_2$-$C_4$-alkylcarbonyl, $C_2$-$C_4$-alkylaminocarbonyl or $C_2$-$C_4$-dialkylaminocarbonyl, or $R^3$ is preferably a phenyl ring, a 5- or 6-membered aromatic heterocyclic ring or a 4-, 5- or 6-membered partly saturated or saturated heterocyclic ring which may contain 1-3 heteroatoms from the group of N, S, O, where the phenyl ring or heterocyclic ring is optionally mono- or polysubstituted identically or differently, and where the substituents may each independently be selected from hydrogen, $C_1$-$C_4$-alkyl, $C_2$-$C_4$-alkenyl, $C_2$-$C_4$-alkynyl, $C_3$-$C_6$-cycloalkyl, $C_1$-$C_4$-haloalkyl, $C_2$-$C_4$-haloalkenyl, $C_2$-$C_4$-haloalkynyl, $C_3$-$C_6$-halocycloalkyl, halogen, cyano, carboxyl, carbamoyl, $NO_2$, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_4$-alkyl)carbonyl, ($C_1$-$C_4$-alkoxy)carbonyl, $R^3$ is more preferably hydrogen or in each case optionally mono- or polysubstituted identically or differently, $C_1$-$C_4$-alkyl, or $C_3$-$C_6$-cycloalkyl, where the substituents may each independently be selected from halogen, cyano, carboxyl, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_2$-$C_4$-alkoxycarbonyl, $C_2$-$C_6$-alkylcarbonyl or a phenyl ring or a 4-, 5- or 6-membered aromatic, partly saturated or saturated heterocyclic ring, where the phenyl ring or heterocyclic ring is optionally mono- or polysubstituted identically or differently, and where the substituents may each independently be selected from hydrogen, $C_1$-$C_4$-alkyl, $C_3$-$C_6$-cycloalkyl, $C_1$-$C_4$-haloalkyl, $C_2$-$C_4$-haloalkenyl, $C_2$-$C_4$-haloalkynyl, $C_3$-$C_6$-halocycloalkyl, halogen, cyano, hydroxyl, $C_1$-$C_4$-alkoxy, $C_1$-$C_4$-haloalkoxy, or $R^3$ is more preferably $C_2$-$C_4$-alkoxycarbonyl, $C_2$-$C_4$-alkylcarbonyl, $C_2$-$C_4$-alkylaminocarbonyl, or $R^3$ is more preferably a phenyl ring, a 5- or 6-membered aromatic heterocyclic ring or a 4-, 5- or 6-membered partly saturated or saturated heterocyclic ring which may contain 1-3 heteroatoms from the group of N, S, O, where the phenyl ring or heterocyclic ring is optionally mono- or polysubstituted identically or differently, and where the substituents may each independently be selected from hydrogen, $C_1$-$C_4$-alkyl, $C_2$-$C_4$-alkenyl, $C_2$-$C_4$-alkynyl, $C_3$-$C_6$-cycloalkyl, $C_1$-$C_4$-haloalkyl, $C_2$-$C_4$-haloalkenyl, $C_2$-$C_4$-haloalkynyl, $C_3$-$C_6$-halocycloalkyl, halogen, cyano, carbamoyl, $NO_2$, hydroxyl, $C_1$-$C_4$-alkoxy, $C_1$-$C_4$-haloalkoxy, or $R^3$ is even more preferably hydrogen, methyl, ethyl, n-propyl, isopropyl, n-butyl, isobutyl, sec-butyl, tert-butyl, cyclopropyl, cyclobutyl, azetidine, oxetane, thietane, pyrrolidine, pyrazolidine, imidazolidine, imidazolidinone, tetrahydrofuran, tetrahydrothiophene, tetrahydrothiophene dioxide, thiazoline, thiazolidine, piperidine, piperazine, tetrahydropyran, dihydrofuranone, dioxane, morpholine, thiomorpholine, thiomorpholine dioxide, phenyl, pyridyl, or $R^3$ is especially preferably hydrogen, methyl, isopropyl, cyclopropyl or tert-butyl.

$R^4$ is preferably hydrogen, $C_1$-$C_4$-alkyl, $C_1$-$C_4$-haloalkyl, halogen, cyano, $C_1$-$C_4$-alkoxy, $C_1$-$C_4$-haloalkoxy, $C_1$-$C_4$-alkylthio or $C_1$-$C_4$-haloalkylthio, two adjacent $R^4$ radicals are likewise preferably —$(CH_2)_3$—, —$(CH_2)_4$—, —$(CH_2)_5$—, —(CH═CH—$)_2$—, —$OCH_2O$—, —$O(CH_2)_2O$—, —$OCF_2O$—, —$(CF_2)_2O$—, —$O(CF_2)_2O$—, —(CH═CH—CH═N)— or —(CH═CH—N═CH)—, $R^4$ is more preferably hydrogen, $C_1$-$C_4$-alkyl, $C_1$-$C_2$-haloalkyl, halogen, cyano or $C_1$-$C_2$-haloalkoxy, two adjacent $R^4$ radicals are more preferably —$(CH_2)_4$—, —(CH═CH—$)_2$—, —$O(CH_2)_2O$—, —$O(CF_2)_2O$—, —(CH═CH—CH═N)— or —(CH═CH—N═CH)—, $R^4$ is even more preferably hydrogen, methyl, trifluoromethyl, cyano, fluorine, chlorine, bromine, iodine or trifluoromethoxy. Even more preferably, two adjacent $R^4$ radicals are also —$(CH_2)_4$—, or —(CH═CH—$)_2$—.

$R^4$ is especially preferably chlorine, fluorine or bromine, $R^4$ is also especially preferably iodine or cyano, two adjacent $R^4$ radicals are especially preferably —(CH═CH—$)_2$ n is preferably 0, 1, 2, n is more preferably 1 or 2, n is even more preferably 1, $R^5$ is preferably $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $R^5$ is more preferably $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluorine, chlorine, bromine, iodine, cyano, nitro or $C_3$-$C_6$-trialkylsilyl, $R^5$ is even more preferably methyl, fluorine, chlorine, bromine or iodine, $R^5$ is especially preferably methyl or chlorine, $Q_X$ is preferably an optionally singly or multiply, identically or differently $R^7$-substituted 5-6 membered heteroaromatic ring which may contain 1-3 heteroatoms from the group of N, O, S, or is phenyl, $Q_X$ is more preferably an optionally singly or multiply, identically or differently $R^7$-substituted, 5- or 6-membered ring selected from the group consisting of furan, thiophene, triazole, imidazole, thiazole, oxazole, isoxazole, isothiazole, thiadiazole, oxadiazole, pyrrole, pyridine, pyrimidine, pyridazine, pyrazine, phenyl or pyrazole, $Q_X$ is even more preferably thiazole, oxazole, pyrrole, imidazole, triazole, pyrimidine, phenyl or pyrazole monosubstituted by the $R^7$ group

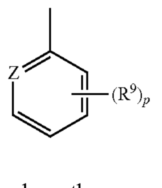

where Z, R and p may have the general definitions specified above or the preferred or more preferred definitions specified below, A is preferably optionally mono- or polysubstituted —($C_1$-$C_4$-alkylene)-, —($C_2$-$C_4$-alkenylene)-, —($C_2$-$C_4$-alkynylene)-, —$R^8$—($C_3$-$C_6$-cycloalkyl)-$R^8$—, —$R^8$—O—$R^8$—, —$R^8$—S—$R^8$—, —$R^8$—S(═O)—$R^8$—, —$R^8$—S(═O$)_2$—$R^8$—, —$R^8$—NH—($C_1$-$C_4$-alkyl)-, —$R^8$—N($C_1$-$C_4$-alkyl)-$R^8$, —$R^8$—C═NO($C_1$-$C_4$-alkyl), —$R^8$—C(═O)—$R^8$, —$R^8$—C(═S)—$R^8$, —$R^8$—C(═O)NH—$R^8$, $R^8$—C(═O)N($C_1$-$C_4$-alkyl)-$R^8$, —$R^8$—S(═O$)_2$NH—$R^8$, —$R^8$—S(═O$)_2$N($C_1$-$C_4$- alkyl)-$R^8$, —$R^8$—NH(C═O)O—$R^8$, —$R^8$—N($C_1$-$C_4$-alkyl)-(C═O)O—$R^8$, —$R^8$—NH(C═O)NH—$R^8$, —$R^8$—NHS(═O$)_2$—$R^8$, —$R^8$—N($C_1$-$C_4$-alkyl)S(═O$)_2$—$R^8$, $R^8$—NH—$R^8$, $R^8$—C(═O)—C(═O)—$R^8$, $R^8$—C(OH)—$R^8$, $R^8$-$Q_Z$-$R^8$, where the substituents may each independently be selected from halogen, cyano, nitro, hydroxyl, $C_1$-$C_6$-alkyl, $C_1$-$C_6$-alkoxy or halogen-$C_1$-$C_6$-alkyl, where $Q_Z$ may have the general definitions specified above or the preferred or more preferred definitions specified below, A is more preferably —$CH_2$—, —$CH_2O$—, —$CH_2OCH_2$—, —$CH_2S$—, —$CH_2SCH_2$—, —$CH_2N$($C_1$-$C_4$-alkyl)-, —$CH_2N$($C_1$-$C_4$-alkyl)$CH_2$—, —CH(Hal)-, —C(Hal$)_2$-, —CH(CN)—, $CH_2$(CO)—, $CH_2$(CS)—, $CH_2$CH(OH)—, -cyclopropyl-, $CH_2$(CO)$CH_2$—, —CH($C_1$-$C_4$-alkyl)-, —C(di-$C_1$-$C_6$-alkyl)-, —$CH_2CH_2$—, —CH═CH—, —C≡C—, —C═NO($C_1$-$C_6$-alkyl), —C(═O)($C_1$-$C_4$-alkyl)-, A is even more preferably —$CH_2$—, —CH($CH_3$), C$(CH_3)_2$, —$CH_2CH_2$—, —CH(CN)—, —$CH_2O$— or —C(═O)—$CH_2$—, A is especially preferably $CH_2$, CH($CH_3$), —$CH_2O$— or —C(═O)—$CH_2$—, $Q_Z$ is preferably a 3- to 4-membered, partly saturated or saturated, or a 5 to 6-membered, partly saturated, saturated or aromatic ring, where the ring may optionally contain 1-3 heteroatoms from the group of N, S, O, where the ring is optionally mono- or polysubstituted identically or differently, and where the substituents may each independently be selected from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $Q_Z$ is more preferably a 3- to 4-membered, partly saturated or saturated, or a 5-membered, partly saturated, saturated or aromatic ring, where the ring may optionally contain 1-2 heteroatoms from the group of N, S, O, where the ring is optionally mono- or polysubstituted identically or differently, and where the substituents may each independently be selected from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $Q_Z$ is even more preferably azetidine, oxetane or thietane, pyrrolidine, pyrroline, pyrazolidine, pyrazoline, imidazolidine, imidazolidone, imidazoline, tetrahydrofuran, tetrahydrothiophene, thiazolidine, isothiazolidine, isoxazoline, which is optionally mono- or polysubstituted identically or differently, and where the substituents may each independently be selected from hydrogen, methyl, ethyl, isopropyl, hydroxyl, methoxy, trifluoromethoxy, fluorine, chlorine, bromine, cyano, difluoromethyl, trifluoromethyl, $R^7$ is preferably $C_1$-$C_6$-alkyl or the radical

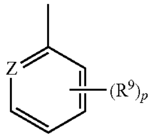

$R^7$ is additionally preferably $C_3$-$C_6$-cycloalkoxy, $R^7$ is more preferably methyl or the radical

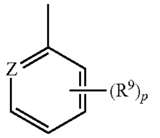

$R^9$ is independently preferably hydrogen, halogen, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$-haloalkylsulphonyl or ($C_1$-$C_4$-alkyl)$C_1$-$C_4$-alkoxyimino, $R^9$ is independently more preferably hydrogen, halogen, cyano or $C_1$-$C_4$-haloalkyl, $R^9$ is independently even more preferably fluorine, chlorine or bromine, $R^9$ is especially preferably chlorine, P is preferably 1, 2 or 3, P is more preferably 1 or 2, P is even more preferably 1, Z is preferably N, CH, CF, CCl, CBr or Cl, Z is more preferably N, CH, CF, CCl or CBr, Z is even more preferably N, CCl or CH, $R^8$ is preferably linear or branched —($C_1$-$C_4$-alkylene)- or a direct bond $R^8$ is more preferably methyl, ethyl, propyl, isopropyl, n-butyl, sec-butyl or isobutyl or a direct bond $R^8$ is even more preferably methyl or ethyl or a direct bond $Q_Y$ is preferably a 5- or 6-membered, partly saturated or saturated heterocyclic or heteroaromatic ring or an aromatic 8-, 9- or 10-membered fused heterobicyclic ring system, where the heteroatoms may be selected from the group of N, S, O, where the ring or ring system is optionally mono- or polysubstituted identically or differently, and where the substituents may each independently be selected from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, carboxyl, carbamoyl, nitro, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, or where the substituents may each independently be selected from phenyl or a 5- or 6-membered heteroaromatic ring, where phenyl or the ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, nitro, hydroxyl, $C_1$-$C_4$-alkoxy, $C_1$-$C_4$-haloalkoxy, $Q_Y$ is more preferably is an optionally mono- or polysubstituted 5- or 6-membered heteroaromatic ring from the group of Q-1 to Q-53 and Q-58 to Q-59, Q62 to Q63, an aromatic 9-membered fused heterobicyclic ring system Q-54 to Q-56 and a 5-membered heterocyclic ring Q-60 to Q-61, where the substituents may each independently be selected from $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy, or where the substituents may each independently be selected from phenyl or einem 5- or 6-membered heteroaromatic ring, where phenyl or the ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, $NO_2$, hydroxyl, $C_1$-$C_4$-alkoxy, $C_1$-$C_4$-haloalkoxy, $Q_Y$ is even more preferably an optionally mono- or polysubstituted 5- or 6-membered heteroaromatic ring from the group of Q-36 to Q-40, Q43, Q-58 to Q-59, Q62, Q63, an aromatic 9-membered fused heterobicyclic ring system Q-54 to Q-56 and a 5-membered heterocyclic ring Q-60 to Q-61, where the substituents may each independently be selected from $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy, or where the substituents may each independently be selected from phenyl or einem 5- or 6-membered heteroaromatic ring, where phenyl or the ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, nitro, $C_1$-$C_4$-alkoxy, $C_1$-$C_4$-haloalkoxy, $Q_Y$ is especially preferably an optionally mono- or polysubstituted identically or differently, heteroaromatic ring from the group of Q-37, Q-38, Q-39, Q-40, Q43, Q-58, Q-59, Q62 and Q63, and a 5-membered heterocyclic ring Q-60, where the substituents may each independently be selected from methyl, ethyl, cyclopropyl, tert-butyl, chlorine, fluorine, iodine, bromine, cyano, nitro, difluoromethyl, trifluoromethyl, pentafluoroethyl, heptafluoro-n-propyl and heptafluoroisopropyl or where the substituents may each independently be selected from phenyl or a 5- or 6-membered heteroaromatic ring, where the substituents may each independently be selected from methyl, ethyl, cyclopropyl, tert-butyl, chlorine, fluorine, iodine, bromine, cyano, nitro, difluoromethyl, trifluoromethyl, pentafluoroethyl, heptafluoro-n-propyl and heptafluoroisopropyl,

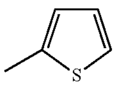

Q-1

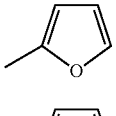

Q-2

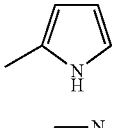

Q-3

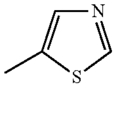

Q-4

-continued
Q-5
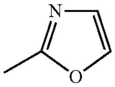
Q-6
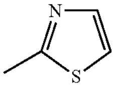
Q-7
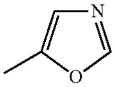
Q-8
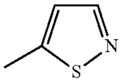
Q-9
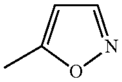
Q-10
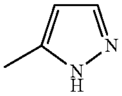
Q-11
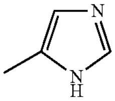
Q-12
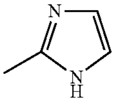
Q-13
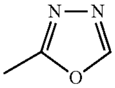
Q-14
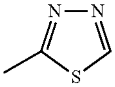
Q-15
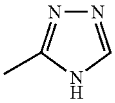
Q-16
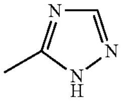
Q-17
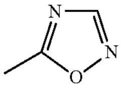
Q-18
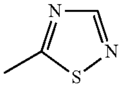
Q-19
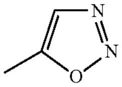
-continued
Q-20
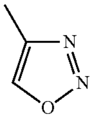
Q-21
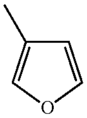
Q-22
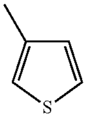
Q-23
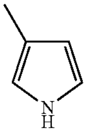
Q-24
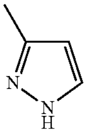
Q-25
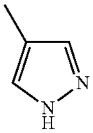
Q-26
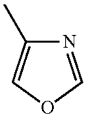
Q-27
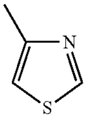
Q-28
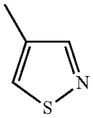
Q-29
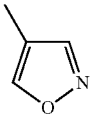
Q-30
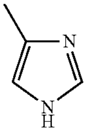
Q-31
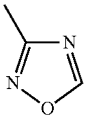

-continued
Q-32
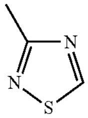
Q-33
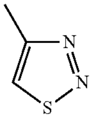
Q-34
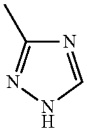
Q-35
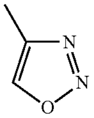
Q-36
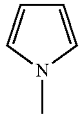
Q-37
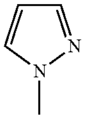
Q-38
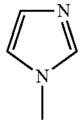
Q-39
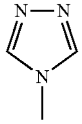
Q-40
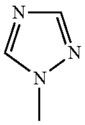
Q-41
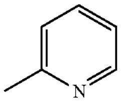
Q-42
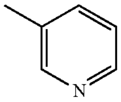
Q-43
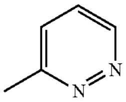
-continued
Q-44
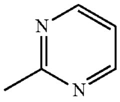
Q-45
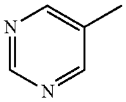
Q-46
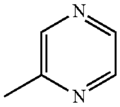
Q-47
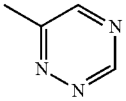
Q-48
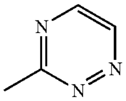
Q-49
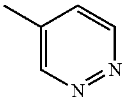
Q-50
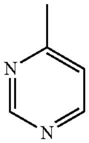
Q-51
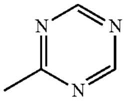
Q-52
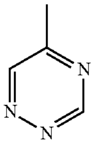
Q-53
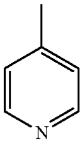
Q-54
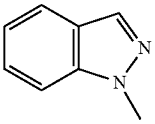
Q-55
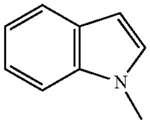

-continued

Q-56

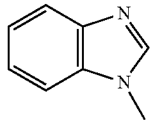

Q-57

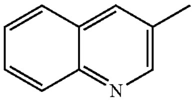

Q-58

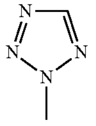

Q-59

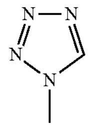

Q-60

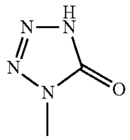

Q-61

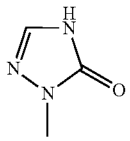

Q-62

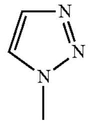

Q-63

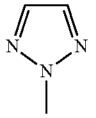

The rings or ring systems shown above may optionally each independently be additionally substituted by oxo, thio, (═O)═NH, (═O)═N—CN, $(═O)_2$. Examples include tetrahydrothiophene dioxide, imidazolidone.

The oxo group as a substituent on a ring carbon atom is then, for example, a carbonyl group in the heterocyclic ring. As a result, lactones and lactams are preferably also included. The oxo group can also occur on the ring heteroatoms which can occur in different oxidation states, for example in the case of N and S, and then form, for example, the divalent groups —N(O)—, —S(O)— (or SO for short) and $—S(O)_2—$ (or $SO_2$ for short) in the heterocyclic ring. In the case of —N(O)— and —S(O)— groups, both enantiomers are included in each case.

Substituents other than the oxo group may also be bonded to a heteroatom on a heterocyclic ring, for example to a nitrogen atom when a hydrogen atom on the nitrogen atom of the base skeleton is replaced. In the case of the nitrogen atom and also of other heteroatoms, for example of the sulphur atom, further substitution to form quarternary ammonium compounds or sulphonium compounds is also a possibility.

More particularly, the compounds of the formula (I) may be present in the form of different regioisomers: for example in the form of mixture of compounds with the definition of Q62 and Q63 or in the form of mixtures of Q58 and Q59. The invention therefore also encompasses active ingredient combinations comprising mixtures of compounds of the formula (I) where $Q_Y$ is defined as Q62 and Q63, and Q58 and Q59, and the compounds may be present in different mixing ratios, and one or more active ingredients from group (II). Preference is given to mixing ratios of compounds of the formula (I) in which the $Q_Y$ radical is Q62 or Q58 to compounds of the formula (I) in which the Qy radical is Q63 or Q59 of 60:40 to 99:1, more preferably of 70:30 to 97:3, even more preferably of 80:20 to 95:5. Especially preferred are the following mixing ratios of a compound of the formula (I) where $Q_Y$ is defined as Q62 or Q58 to the compound of the formula (I) where $Q_Y$ is defined as Q63 or Q59: 80:20; 81:19; 82:18; 83:17; 84:16; 85:15, 86:14; 87:13; 88:12; 89:11; 90:10, 91:9; 92:8; 93:7; 96:6; 95:5.

Additionally preferred are active ingredient combinations comprising at least one active ingredient of the formula (I-1)

(I-1)

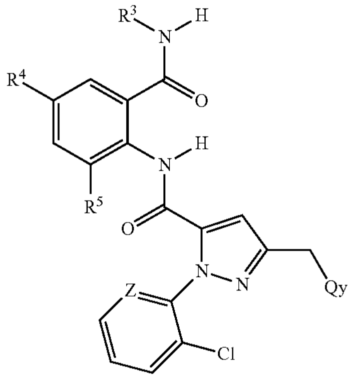

in which $R^3$ is hydrogen or in each case optionally mono- or polysubstituted identically or differently, $C_1$-$C_6$-alkyl, $C_1$-$C_6$-alkoxy, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl, where the substituents may each independently be selected from halogen, amino, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_2$-$C_6$-alkoxycarbonyl, $C_1$-$C_6$-alkylcarbonyl $C_3$-$C_6$-cycloalkylamino or a 5- or 6-membered heteroaromatic ring, $R^4$ is halogen, cyano or methyl, $R^5$ is methyl or chlorine, Z is N, CCl or CH, Qy an optionally mono- or polysubstituted 5- or 6-membered heteroaromatic ring from the group of Q-36 to Q-40, Q43, Q-58 to Q-59, Q62, Q63, an aromatic 9-membered fused heterobicyclic ring system Q-54 to Q-56 and a 5-membered heterocyclic ring Q-60 to Q-61, where the substituents may each independently be selected from $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy, where the compounds of the formula (I-1) may be present in the form of salts, and one or more active ingredients selected from group (II).

More preferred combinations are those comprising at least one of the active ingredients of the formula (I-1) specified as preferred, more preferred, even more preferred or especially preferred, and one or more active ingredients selected from group (II).

Preferred, more preferred, even more preferred or especially preferred active ingredients are those of the formula (I-1) where $R^3$ is preferably hydrogen or in each case optionally mono- or polysubstituted identically or differently, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, where the substituents may each independently be selected from halogen, cyano, amino, hydroxyl, $C_1$-$C_6$-alkyl, $C_1$-$C_4$-alkoxy, $C_1$-$C_4$-haloalkoxy, $C_1$-$C_4$-alkylthio, $C_3$-$C_6$-cycloalkyl, a 5- or 6-membered heteroaromatic ring containing 1-2 heteroatoms from the group of N, O, S, where no two oxygen atoms in the ring are adjacent, $R^3$ is more preferably one of the following radicals:

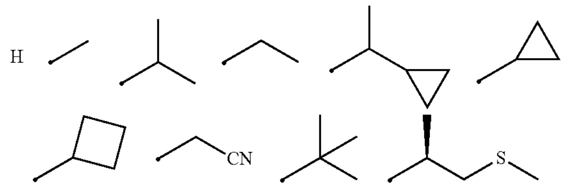

$R^4$ is preferably halogen, cyano or methyl, $R^4$ is more preferably chlorine and cyano, $R^4$ is likewise more preferably bromine, fluorine, iodine or methyl, $R^5$ is preferably and more preferably methyl, Z is preferably N or CH, $Q_Y$ is preferably an optionally mono- or polysubstituted identically or differently, heteroaromatic ring from the group of Q-37, Q-38, Q-39, Q-40, Q43, Q-58, Q-59, Q62 and Q63, and a 5-membered heterocyclic ring Q-60, where the substituents may each independently be selected from methyl, ethyl, cyclopropyl, tert-butyl, chlorine, fluorine, iodine, bromine, cyano, nitro, difluoromethyl, trifluoromethyl, pentafluoroethyl, heptafluoro-n-propyl and heptafluoroisopropyl.

$Q_Y$ is more preferably an optionally mono- or polysubstituted identically or differently, heteroaromatic ring from the group of Q-58 and Q-59, where the substituents may each independently be selected from methyl, ethyl, cyclopropyl, tert-butyl, difluoromethyl, trifluoromethyl, pentafluoroethyl, n-heptafluoropropyl and isoheptafluoropropyl.

More particularly, the compounds of the formula (I-1) may be present in the form of different regioisomers, for example in the form of mixtures of compounds with the definition of Q62 and Q63 or in the form of mixtures of Q58 and Q59. The invention therefore also includes active ingredient combinations comprising mixtures of compounds of the formula (I-1) where $Q_Y$ is defined as Q62 and Q63, and Q58 and Q59, and the compounds may be present in different mixing ratios, and one or more active ingredients from the group (II). Preference is given to mixing ratios of compounds of the formula (I) in which the $Q_Y$ radical is Q62 or Q58 to compounds of the formula (I) in which the Qy radical is Q63 or Q59 of 60:40 to 99:1, more preferably of 70:30 to 97:3, even more preferably of 80:20 to 95:5. Especially preferred are the following mixing ratios of a compound of the formula (I) where $Q_Y$ is defined as Q62 or Q58 to the compound of the formula (I) where $Q_Y$ is defined as Q63 or Q59: 80:20; 81:19; 82:18; 83:17; 84:16; 85:15, 86:14; 87:13; 88:12; 89:11; 90:10, 91:9; 92:8; 93:7; 96:6; 95:5.

Additionally preferred are active ingredient combinations comprising at least one active ingredient of the general formula (I) or (I-1) and an active ingredient from group (II) selected from acrinathrin
alpha-cypermethrin
betacyfluthrin
cyhalothrin
cypermethrin
deltamethrin
esfenvalerate
etofenprox
fenpropathrin
fenvalerate
flucythrinate
lambda-cyhalothrin
gamma-cyhalothrin
permethrin
tau-fluvalinate
transfluthrin
zeta-cypermethrin
cyfluthrin
bifenthrin
tefluthrin
eflusilanate
fubfenprox
pyrethrin
resmethrin
imidacloprid
acetamiprid
thiamethoxam
nitenpyram
thiacloprid
dinotefuran
clothianidin
imidaclothiz
chlorfluazuron
diflubenzuron
lufenuron
teflubenzuron
triflumuron
novaluron
flufenoxuron
hexaflumuron
bistrifluoron
noviflumuron
buprofezin
cyromazine
methoxyfenozide
tebufenozide
halofenozide
chromafenozide
endosulfan
fipronil
ethiprole
pyrafluprole
pyriprole
flubendiamide
chlorantraniliprole (Rynaxypyr)
cyazypyr
emamectin
emamectin benzoate
abamectin
ivermectin milbemectin
lepimectin
tebufenpyrad
fenpyroximate
pyridaben
fenazaquin
pyrimidifen
tolfenpyrad
dicofol
cyenopyrafen
cyflumetofen
acequinocyl
fluacrypyrin
bifenazate
diafenthiuron
etoxazole
clofentezine
spinosad
triarathen
tetradifon
propargite
hexythiazox
bromopropylate
chinomethionat
amitraz
pyrifluquinazone
pymetrozine
flonicamid
pyriproxyfen
diofenolan
chlorfenapyr
metaflumizone
indoxacarb
chlorpyrifos
spirodiclofen
spiromesifen
spirotetramat
pyridalyl
spinetoram
acephate
triazophos
profenofos
fenamiphos
4-{[(6-chloropyrid-3-yl)methyl](2,2-difluro-ethyl)amino}furan-2(5H)-one
cadusaphos
carbaryl
carbofuran
ethoprophos
thiodicarb
aldicarb
metamidophos
methiocarb
sulfoxaflor Additionally likewise preferred are active ingredient combinations comprising at least one active ingredient of the general formula (I) or (I-1) and an active ingredient of group (II) selected from

*Bacillus firmus* I-1582
dichloropropene
dimethoate
metaldehyde
methomyl
cartap
oil (for example petroleum)
chloropicrin
carbosulfan
dichlorvos
metam-sodium
phoxim
monocrotophos
oxamyl
methidathion
fenitrothion
terbufos
fluensulfone
imicyafos
11-(4-chloro-2,6-dimethylphenyl)-12-hydroxy-1,4-dioxa-9-azadispiro[4.2.4.2]tetradec-11en-10-one
2-{6-[2-(5-fluropyridin-3-yl)-1,3-thiazol-5-yl]pyridin-2-yl}pyrimidine Additionally more preferred are active ingredient combinations comprising at least one active ingredient of the general formula (I) or (I-1) and an active ingredient from group (II) selected from acrinathrin
alpha-cypermethrin
betacyfluthrin
cyhalothrin
cypermethrin
deltamethrin
lambda-cyhalothrin
gamma-cyhalothrin
transfluthrin
cyfluthrin
bifenthrin
tefluthrin
imidacloprid
acetamiprid
thiamethoxam
thiacloprid
dinotefuran
clothianidin
lufenuron
triflumuron
novaluron
flufenoxuron
buprofezin
methoxyfenozide
tebufenozide
fipronil
ethiprole
flubendiamide
chlorantraniliprole (Rynaxypyr)
cyazypyr
emamectin
emamectin benzoate
abamectin
milbemectin
tebufenpyrad
fenpyroximate
diafenthiuron
spinosad
flonicamid
chlorfenapyr
metaflumizone
indoxacarb
chlorpyrifos
spirodiclofen
spiromesifen
spirotetramat
pyridalyl
spinetoram
acephate triazophos
profenofos
fenamiphos
4-{[(6-chloropyrid-3-yl)methyl](2,2-difluoro-ethyl)amino}furan-2(5H)-one
cadusaphos
carbaryl
carbofuran
ethoprophos
thiodicarb
aldicarb
metamidophos
methiocarb
sulfoxaflor Additionally likewise more preferred are active ingredient combinations comprising at least one active ingredient of the general formula (I) or (I-1) and an active ingredient from group (II) selected from

*Bacillus firmus* I-1582
dichloropropene
dimethoate
methomyl
imicyafos
fluensulfone
11-(4-chloro-2,6-dimethylphenyl-12-hydroxy-1,4-dioxa-9-azadispiro[4.2.4.2]tetradec-11-en-10-one
2-{6-[2-(5-fluoropyridin-3-yl)-1,3-thiazol-5-yl]pyridin-2-yl}pyrimidine Even more preferred active ingredient combinations comprise exactly one active ingredient of the formula (I-1-1) to (I-1-60) and one or more active ingredients from group (II).

(I-1-1)

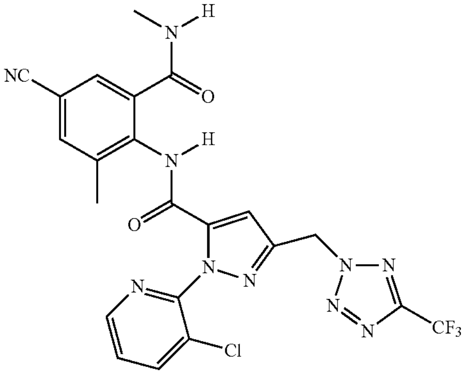

(I-1-2)

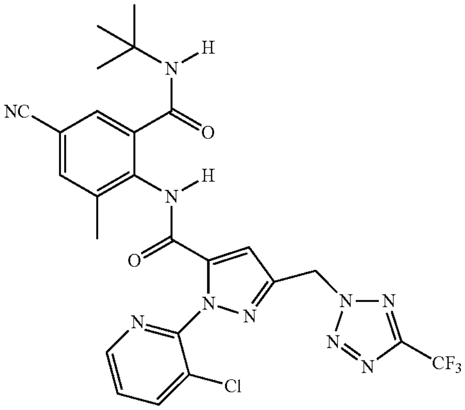

-continued (I-1-3)

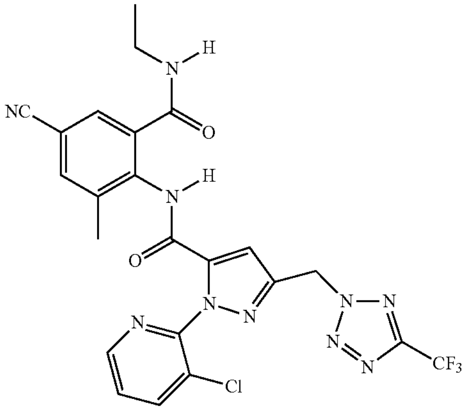

(I-1-4)

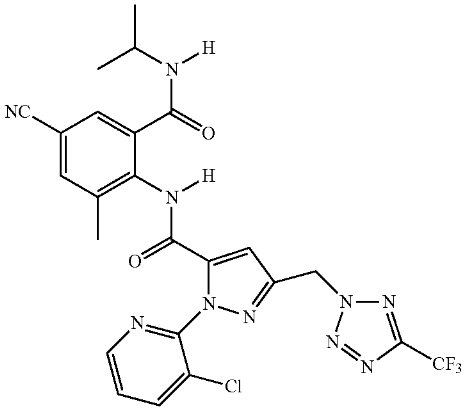

(I-1-5)

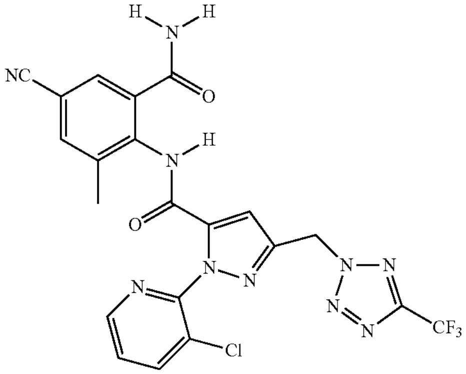

(I-1-6)

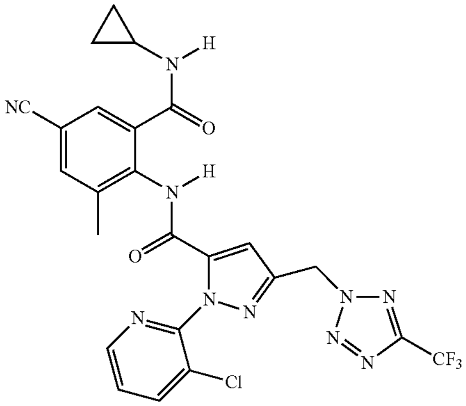

-continued
(I-1-7)
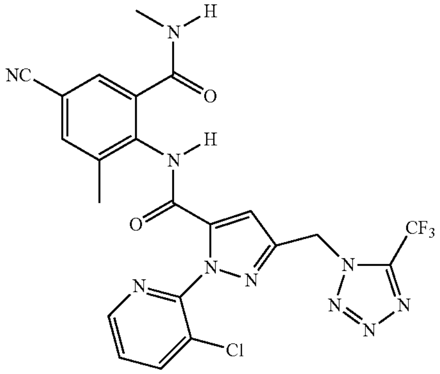
(I-1-8)
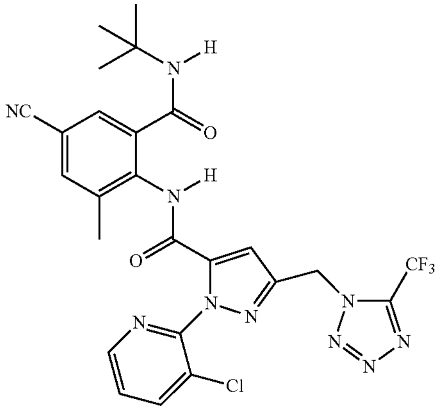
(I-1-9)
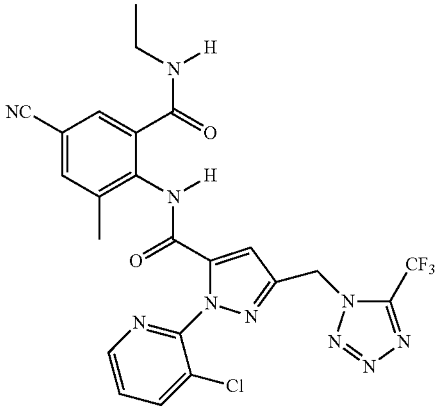
(I-1-10)
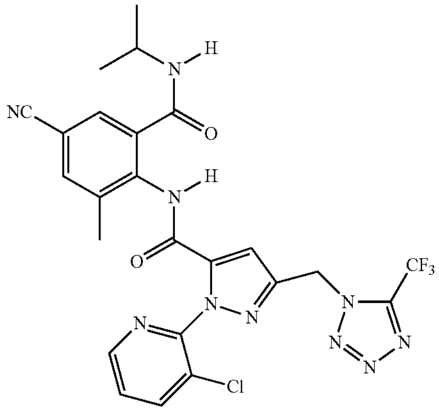
-continued
(I-1-11)
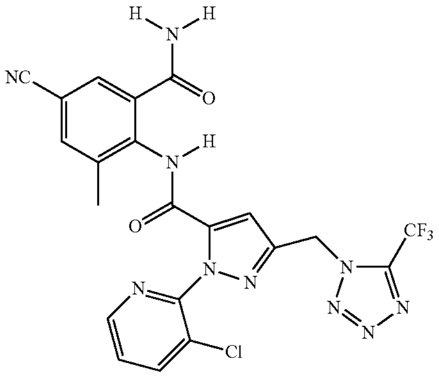
(I-1-12)
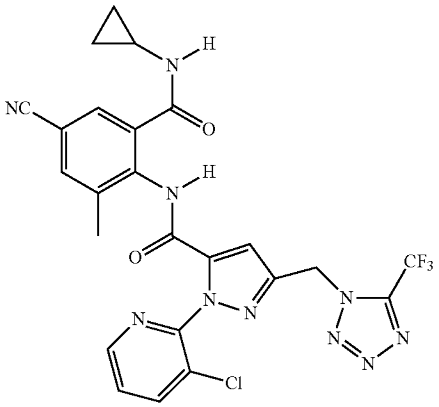
(I-1-13)
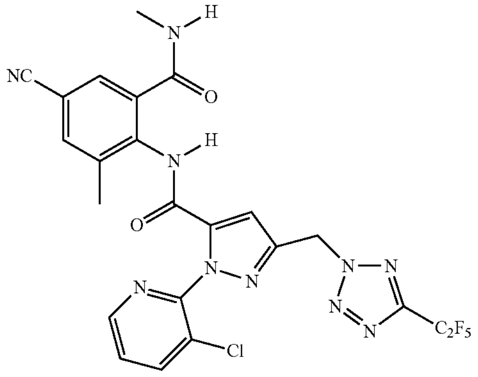
(I-1-14)
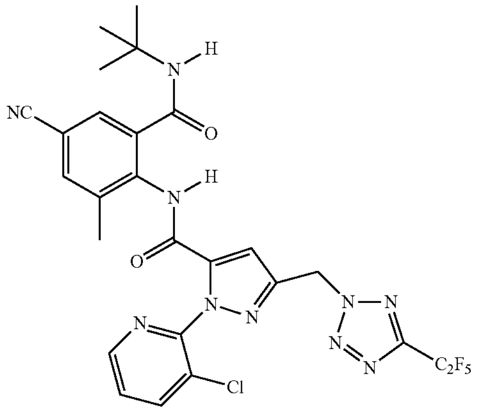

-continued
(I-1-15)
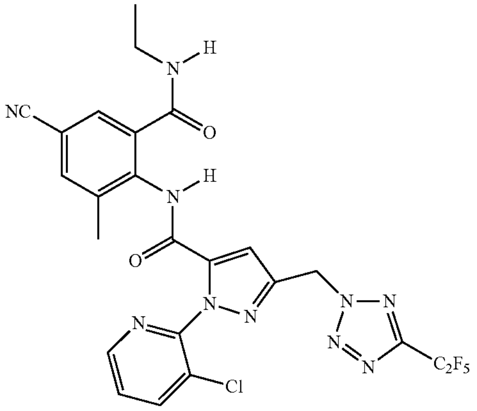
(I-1-16)
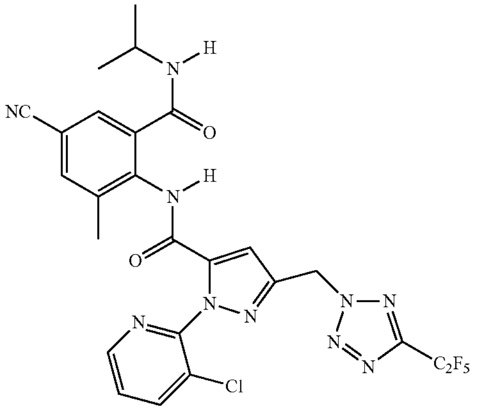
(I-1-17)
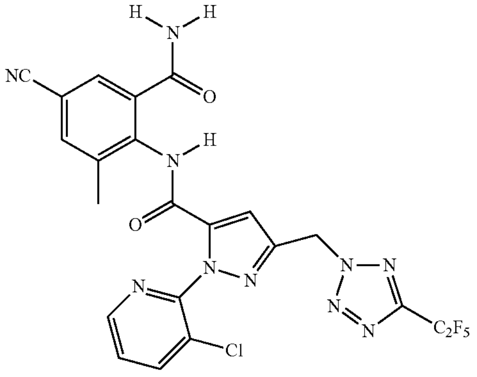
(I-1-18)
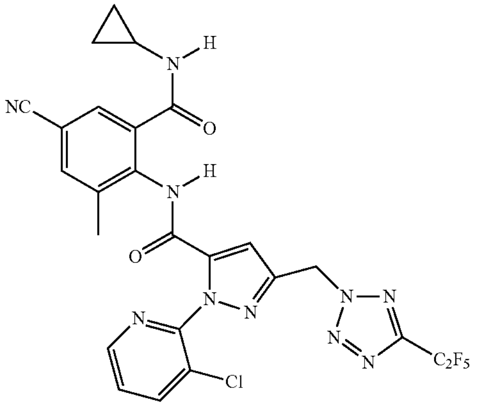
-continued
(I-1-19)
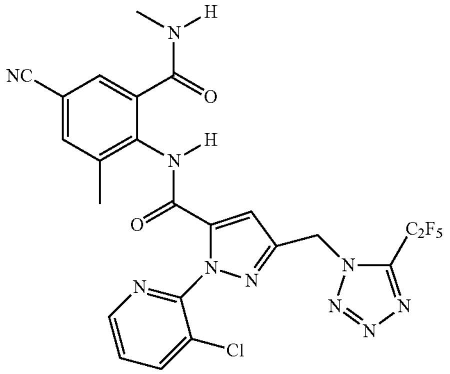
(I-1-20)
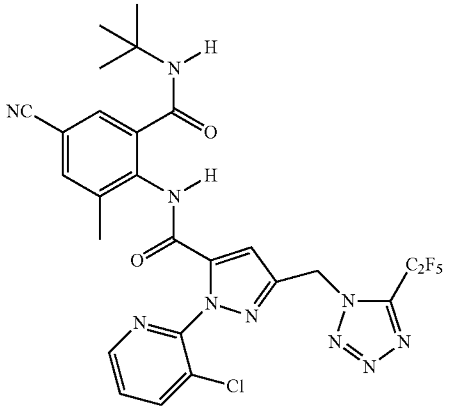
(I-1-21)
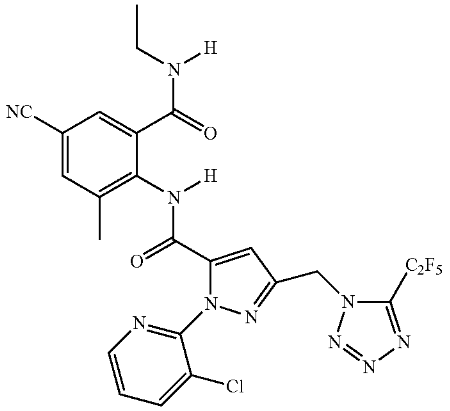
(I-1-22)
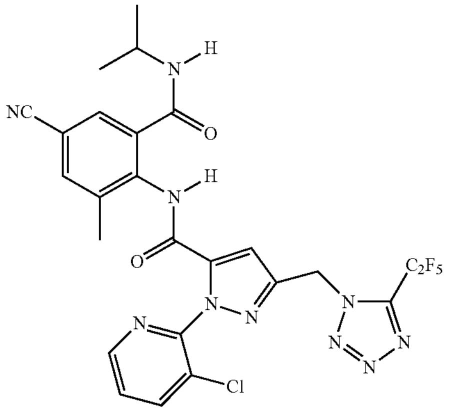

-continued
(I-1-23)
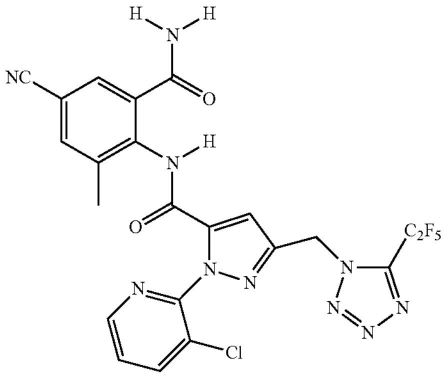
(I-1-24)
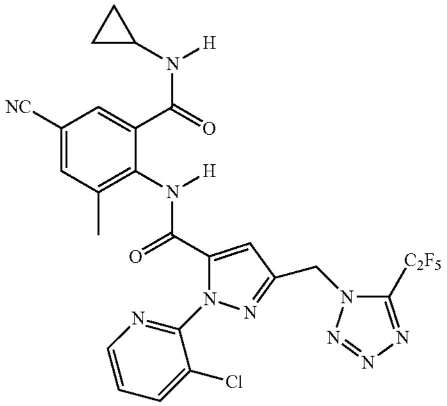
(I-1-25)
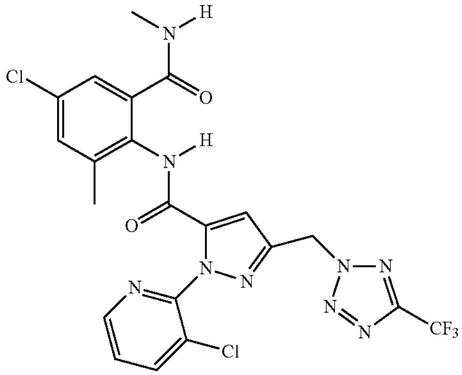
(I-1-26)
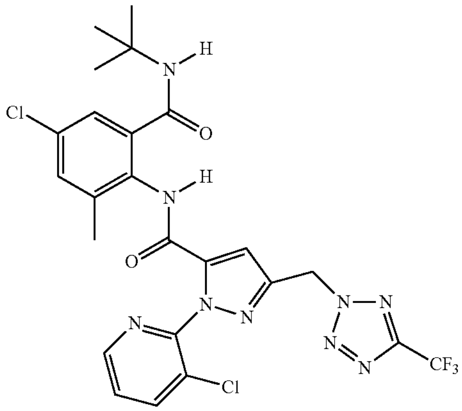
-continued
(I-1-27)
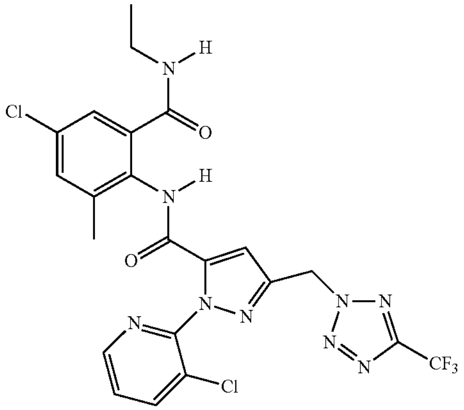
(I-1-28)
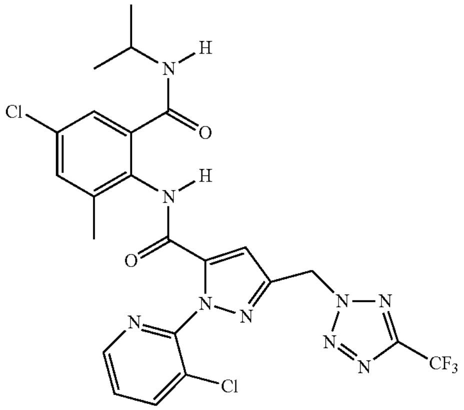
(I-1-29)
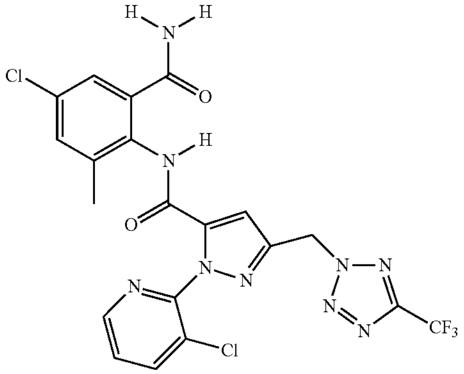
(I-1-30)
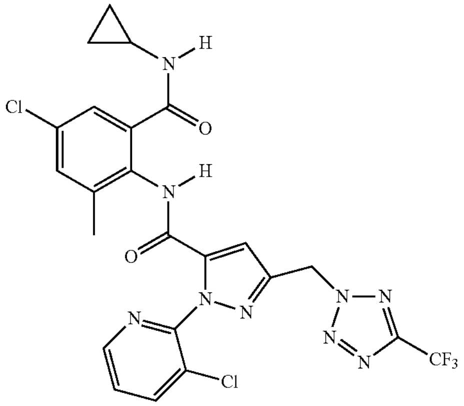

-continued
(I-1-31)
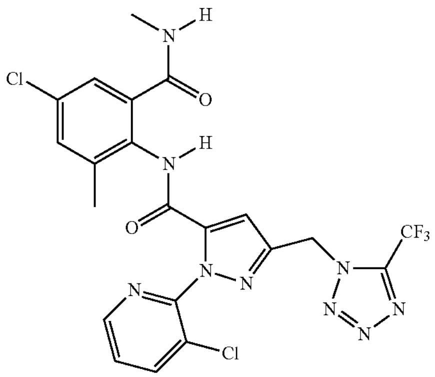
(I-1-32)
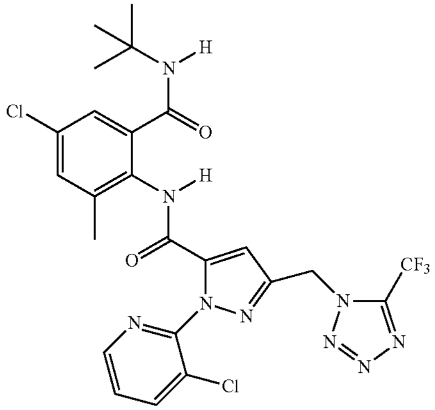
(I-1-33)
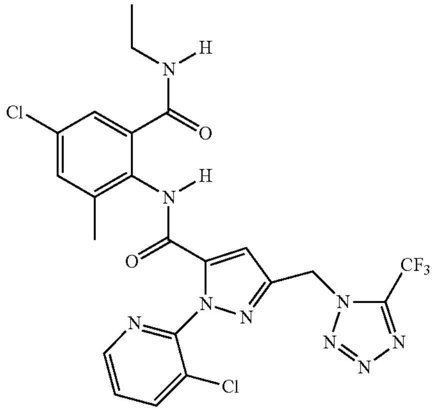
(I-1-34)
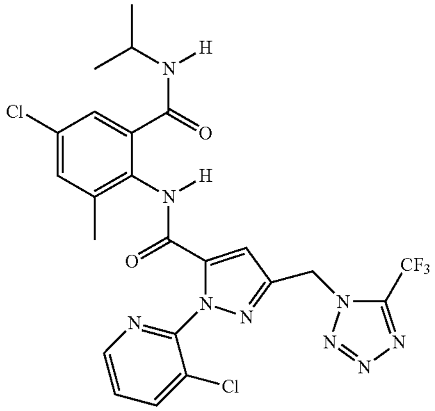
-continued
(I-1-35)
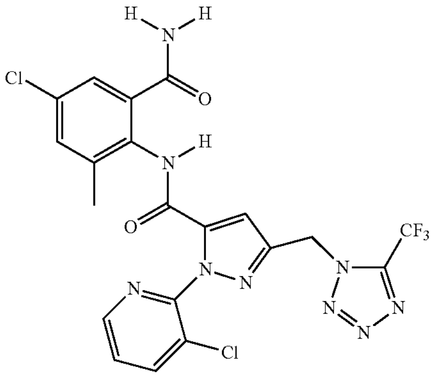
(I-1-36)
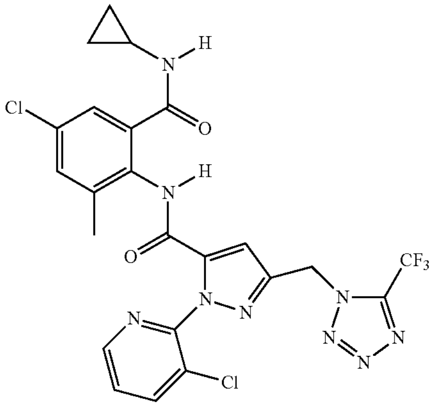
(I-1-37)
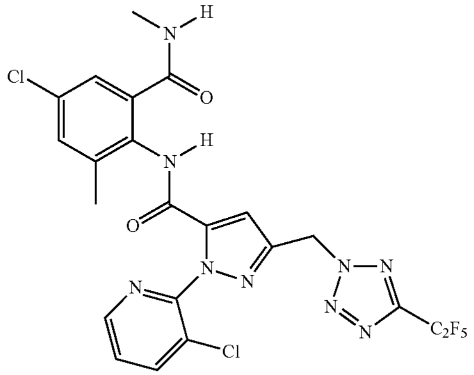
(I-1-38)
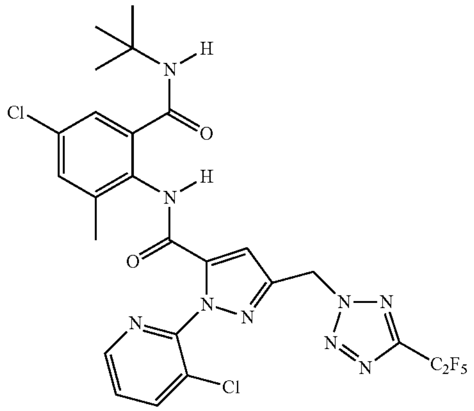

-continued
(I-1-39)
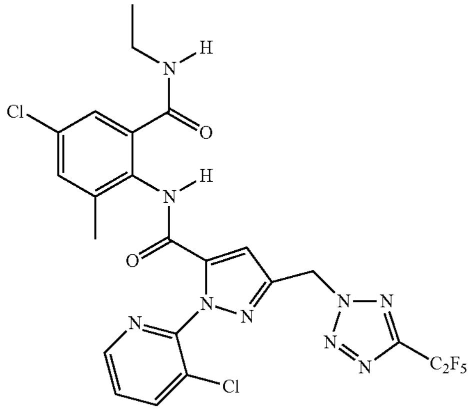
(I-1-40)
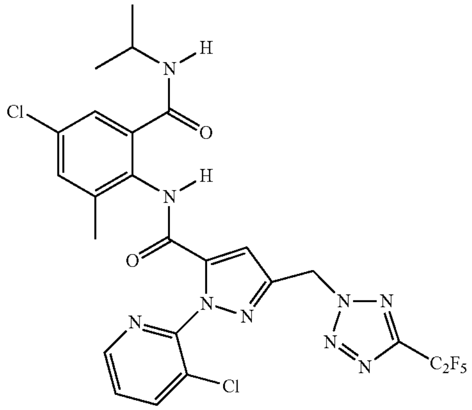
(I-1-41)
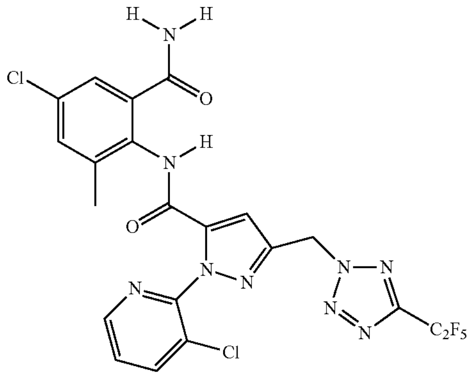
(I-1-42)
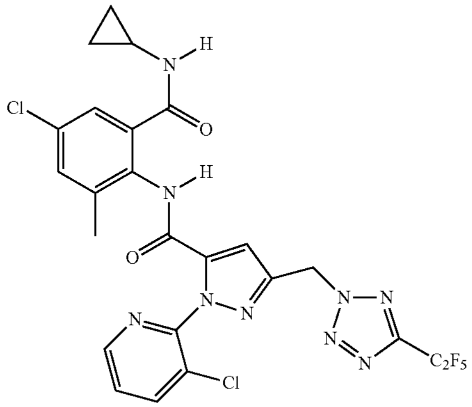
-continued
(I-1-43)
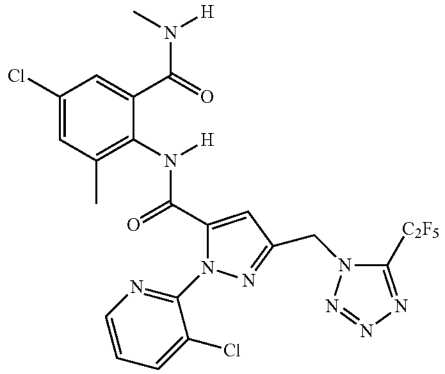
(I-1-44)
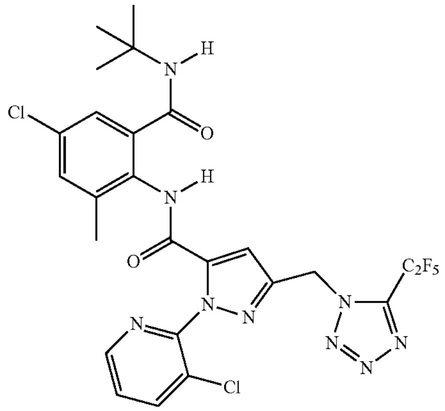
(I-1-45)
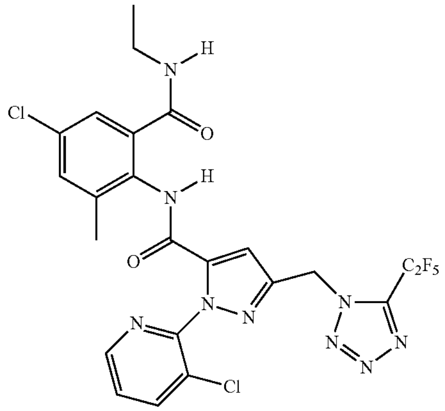
(I-1-46)
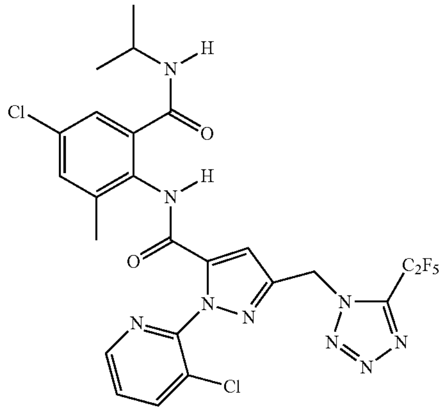

-continued
(I-1-47)
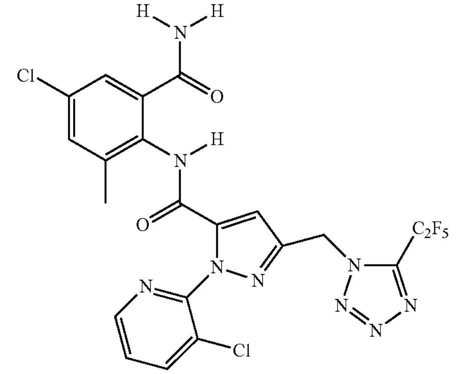
(I-1-48)
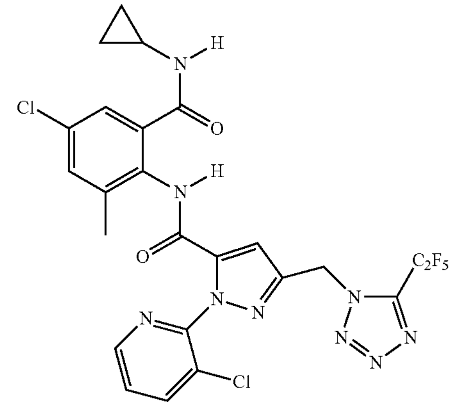
(I-1-49)
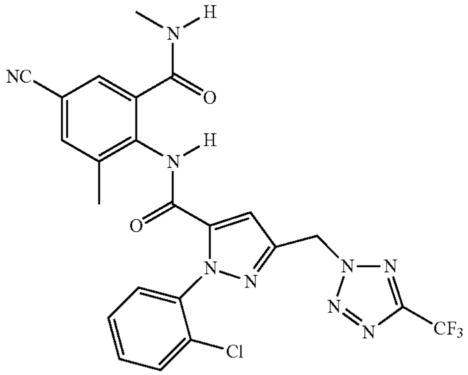
(I-1-50)
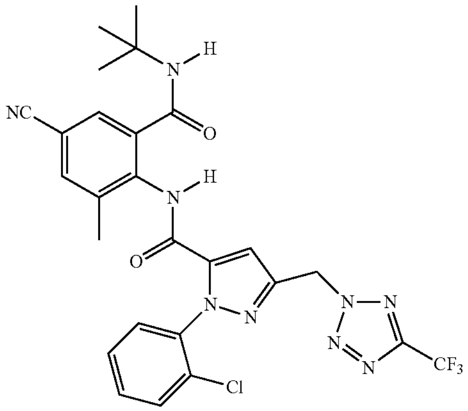
-continued
(I-1-51)
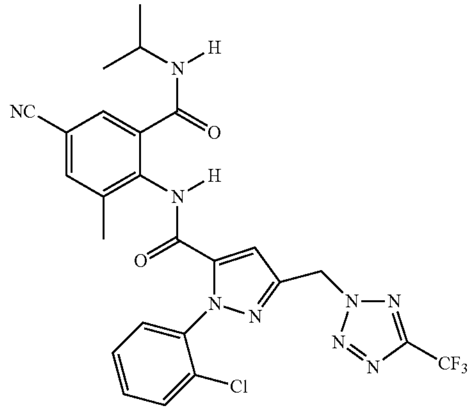
(I-1-52)
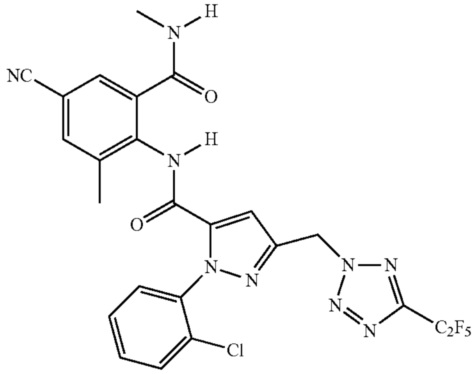
(I-1-53)
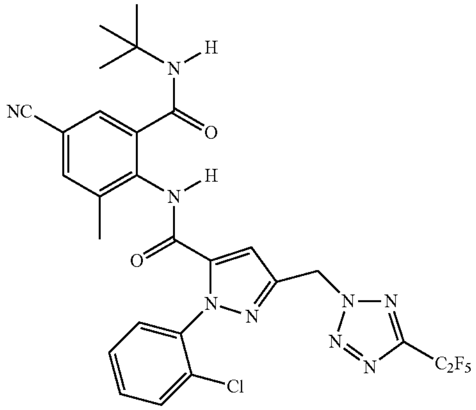
(I-1-54)
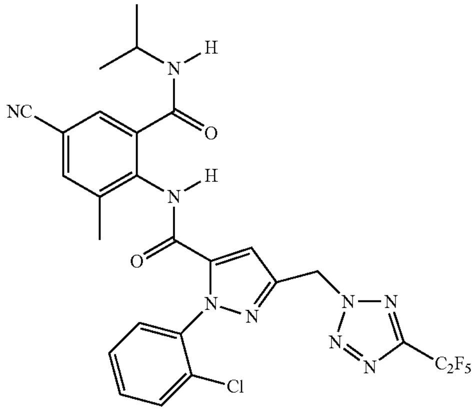

-continued (I-1-55)

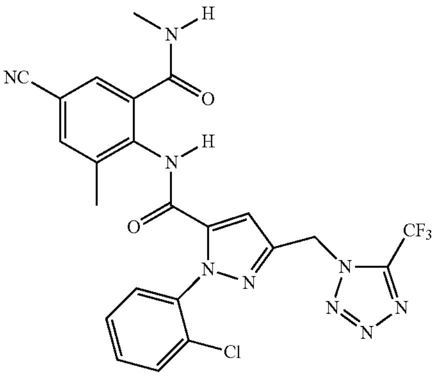

(I-1-56)

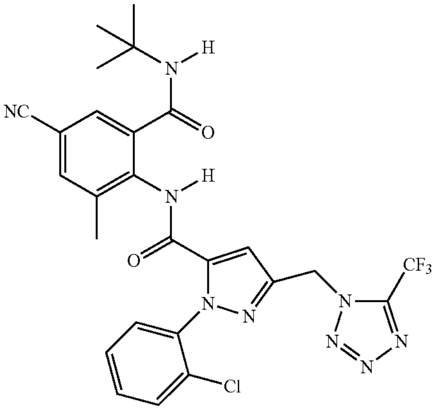

(I-1-57)

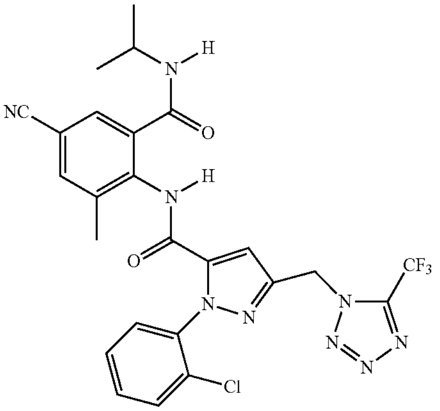

(I-1-58)

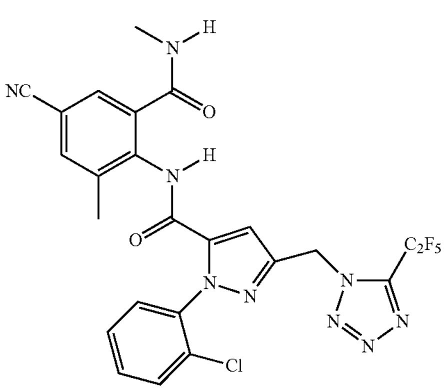

-continued (I-1-59)

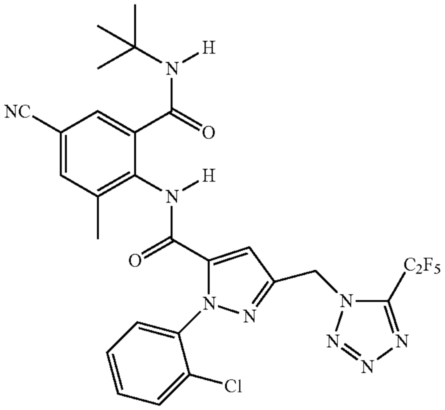

(I-1-60)

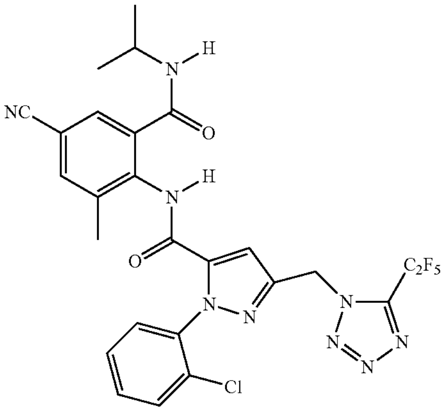

Additionally even more preferred active ingredient combinations comprise the mixtures of active ingredients of the formula (I-1-1) to (I-1-60) and one or more active ingredients from group (II) specified hereinafter.

These mixtures are present preferably in a mixing ratio of 80:20 to 99:1. Mention should be made by way of example of the mixture I-1-1/I-1-7, the compound of the formula I-1-1 being present relative to the compound of the formula I-1-7 in a mixing ratio of 80:20 to 99:1. Mention should likewise be made by way of example of the mixture 1-1-2/1-1-8, the compound of the formula I-1-2 being present relative to the compound of the formula I-1-8 in a mixing ratio of 80:20 to 99:1.

I-1-1-/1-1-7,
1-1-2/1-1-8,
1-1-3/1-1-9,
I-1-4/1-1-10,
I-1-5/1-1-11,
I-1-6/1-1-12,
I-1-13/I-1-1-19,
1-1-14/1-1-20,
I-1-15/I-1-21,
I-1-16/I-1-22,
I-1-17/I-1-23,
I-1-18/I-1-24,
1-1-25/1-1-31,
1-1-26/1-1-32,
I-1-27/I-1-33,
1-1-28/1-1-34,
I-1-29/I-1-35,
I-1-30/I-1-36,
1-1-37/1-1-43, 1-1-38/1-1-44,
I-1-39/I-1-45,
I-1-40/I-1-46,
I-1-41/I-1-47,
I-1-42/I-1-48,
I-1-49/I-1-55,
I-1-50/I-1-56,
I-1-51/I-1-57,
I-1-52/I-1-58,
I-1-53/I-1-59,
I-1-54/I-1-60.

Especially preferred are combinations comprising the active ingredient (I-1-1) and exactly one active ingredient from group II in the mixing ratios specified in Table 1.

Especially preferred are combinations comprising the active ingredient (I-1-2) and exactly one active ingredient from group II in the mixing ratios specified in Table 1.

Especially preferred are combinations comprising the active ingredient (I-1-3) and exactly one active ingredient from group II in the mixing ratios specified in Table 1.

Especially preferred are combinations comprising the active ingredient (I-1-4) and exactly one active ingredient from group II in the mixing ratios specified in Table 1.

Especially preferred are combinations comprising the active ingredient (I-1-5) and exactly one active ingredient from group II in the mixing ratios specified in Table 1.

Especially preferred are combinations comprising the active ingredient (I-1-6) and exactly one active ingredient from group II in the mixing ratios specified in Table 1.

Especially preferred are combinations comprising the active ingredient (I-1-7) and exactly one active ingredient from group II in the mixing ratios specified in Table 1.

Especially preferred are combinations comprising the active ingredient (I-1-8) and exactly one active ingredient from group II in the mixing ratios specified in Table 1.

Especially preferred are combinations comprising the active ingredient (I-1-9) and exactly one active ingredient from group II in the mixing ratios specified in Table 1.

Especially preferred are combinations comprising the active ingredient (I-1-10) and exactly one active ingredient from group II in the mixing ratios specified in Table 1.

Especially preferred are combinations comprising the active ingredient (I-1-11) and exactly one active ingredient from group II in the mixing ratios specified in Table 1.

Especially preferred are combinations comprising the active ingredient (I-1-12) and exactly one active ingredient from group II in the mixing ratios specified in Table 1.

Especially preferred are combinations comprising the active ingredient (I-1-13) and exactly one active ingredient from group II in the mixing ratios specified in Table 1.

Especially preferred are combinations comprising the active ingredient (I-1-14) and exactly one active ingredient from group II in the mixing ratios specified in Table 1.

Especially preferred are combinations comprising the active ingredient (I-1-15) and exactly one active ingredient from group II in the mixing ratios specified in Table 1.

Especially preferred are combinations comprising the active ingredient (I-1-16) and exactly one active ingredient from group II in the mixing ratios specified in Table 1.

Especially preferred are combinations comprising the active ingredient (I-1-17) and exactly one active ingredient from group II in the mixing ratios specified in Table 1.

Especially preferred are combinations comprising the active ingredient (I-1-18) and exactly one active ingredient from group II in the mixing ratios specified in Table 1.

Especially preferred are combinations comprising the active ingredient (I-1-19) and exactly one active ingredient from group II in the mixing ratios specified in Table 1.

Especially preferred are combinations comprising the active ingredient (I-1-20) and exactly one active ingredient from group II in the mixing ratios specified in Table 1.

Especially preferred are combinations comprising the active ingredient (I-1-21) and exactly one active ingredient from group II in the mixing ratios specified in Table 1.

Especially preferred are combinations comprising the active ingredient (I-1-22) and exactly one active ingredient from group II in the mixing ratios specified in Table 1.

Especially preferred are combinations comprising the active ingredient (I-1-23) and exactly one active ingredient from group II in the mixing ratios specified in Table 1.

Especially preferred are combinations comprising the active ingredient (I-1-24) and exactly one active ingredient from group II in the mixing ratios specified in Table 1.

Especially preferred are combinations comprising the active ingredient (I-1-25) and exactly one active ingredient from group II in the mixing ratios specified in Table 1.

Especially preferred are combinations comprising the active ingredient (I-1-26) and exactly one active ingredient from group II in the mixing ratios specified in Table 1.

Especially preferred are combinations comprising the active ingredient (I-1-27) and exactly one active ingredient from group II in the mixing ratios specified in Table 1.

Especially preferred are combinations comprising the active ingredient (I-1-28) and exactly one active ingredient from group II in the mixing ratios specified in Table 1.

Especially preferred are combinations comprising the active ingredient (I-1-29) and exactly one active ingredient from group II in the mixing ratios specified in Table 1.

Especially preferred are combinations comprising the active ingredient (I-1-30) and exactly one active ingredient from group II in the mixing ratios specified in Table 1.

Especially preferred are combinations comprising the active ingredient (I-1-31) and exactly one active ingredient from group II in the mixing ratios specified in Table 1.

Especially preferred are combinations comprising the active ingredient (I-1-32) and exactly one active ingredient from group II in the mixing ratios specified in Table 1.

Especially preferred are combinations comprising the active ingredient (I-1-33) and exactly one active ingredient from group II in the mixing ratios specified in Table 1.

Especially preferred are combinations comprising the active ingredient (I-1-34) and exactly one active ingredient from group II in the mixing ratios specified in Table 1.

Especially preferred are combinations comprising the active ingredient (I-1-35) and exactly one active ingredient from group II in the mixing ratios specified in Table 1.

Especially preferred are combinations comprising the active ingredient (I-1-36) and exactly one active ingredient from group II in the mixing ratios specified in Table 1.

Especially preferred are combinations comprising the active ingredient (I-1-37) and exactly one active ingredient from group II in the mixing ratios specified in Table 1.

Especially preferred are combinations comprising the active ingredient (I-1-38) and exactly one active ingredient from group II in the mixing ratios specified in Table 1.

Especially preferred are combinations comprising the active ingredient (I-1-39) and exactly one active ingredient from group II in the mixing ratios specified in Table 1.

Especially preferred are combinations comprising the active ingredient (I-1-40) and exactly one active ingredient from group II in the mixing ratios specified in Table 1.

Especially preferred are combinations comprising the active ingredient (I-1-41) and exactly one active ingredient from group II in the mixing ratios specified in Table 1.

Especially preferred are combinations comprising the active ingredient (I-1-42) and exactly one active ingredient from group II in the mixing ratios specified in Table 1.

Especially preferred are combinations comprising the active ingredient (I-1-43) and exactly one active ingredient from group II in the mixing ratios specified in Table 1.

Especially preferred are combinations comprising the active ingredient (I-1-44) and exactly one active ingredient from group II in the mixing ratios specified in Table 1.

Especially preferred are combinations comprising the active ingredient (I-1-45) and exactly one active ingredient from group II in the mixing ratios specified in Table 1.

Especially preferred are combinations comprising the active ingredient (I-1-46) and exactly one active ingredient from group II in the mixing ratios specified in Table 1.

Especially preferred are combinations comprising the active ingredient (I-1-47) and exactly one active ingredient from group II in the mixing ratios specified in Table 1.

Especially preferred are combinations comprising the active ingredient (I-1-48) and exactly one active ingredient from group II in the mixing ratios specified in Table 1.

Especially preferred are combinations comprising the active ingredient (I-1-49) and exactly one active ingredient from group II in the mixing ratios specified in Table 1.

Especially preferred are combinations comprising the active ingredient (I-1-50) and exactly one active ingredient from group II in the mixing ratios specified in Table 1.

Especially preferred are combinations comprising the active ingredient (I-1-51) and exactly one active ingredient from group II in the mixing ratios specified in Table 1.

Especially preferred are combinations comprising the active ingredient (I-1-52) and exactly one active ingredient from group II in the mixing ratios specified in Table 1.

Especially preferred are combinations comprising the active ingredient (I-1-53) and exactly one active ingredient from group II in the mixing ratios specified in Table 1.

Especially preferred are combinations comprising the active ingredient (I-1-54) and exactly one active ingredient from group II in the mixing ratios specified in Table 1.

Especially preferred are combinations comprising the active ingredient (I-1-55) and exactly one active ingredient from group II in the mixing ratios specified in Table 1.

Especially preferred are combinations comprising the active ingredient (I-1-56) and exactly one active ingredient from group II in the mixing ratios specified in Table 1.

Especially preferred are combinations comprising the active ingredient (I-1-57) and exactly one active ingredient from group II in the mixing ratios specified in Table 1.

Especially preferred are combinations comprising the active ingredient (I-1-58) and exactly one active ingredient from group II in the mixing ratios specified in Table 1.

Especially preferred are combinations comprising the active ingredient (I-1-59) and exactly one active ingredient from group II in the mixing ratios specified in Table 1.

Especially preferred are combinations comprising the active ingredient (I-1-60) and exactly one active ingredient from group II in the mixing ratios specified in Table 1.

The active ingredient combinations may additionally also comprise further fungicidally, acaricidally or insecticidally active mixture components.

When the active ingredients are present in particular weight ratios in the inventive active ingredient combinations, the improved effect is manifested. However, the weight ratios of the active ingredients in the active ingredient combinations can be varied within a relatively wide range. In general, the inventive combinations comprise active ingredients of the formula (I) to the mixing partner from group (II) in a ratio of 625:1 to 1:625; preferably in the preferred and more preferred mixing ratios specified in Table 1 below:

the mixing ratios are based on weight ratios. The ratio should be understood as the active ingredient of the formula (I):mixing partner to active ingredient of the formula (I):mixing partner.

| | Mixing partner | Preferred mixing ratio | More preferred mixing ratio | Most preferred mixing ratio |
|---|---|---|---|---|
| 1. | acrinathrin | 125:1 to 1:125 | 25:1 to 1:25 | 5:1 to 1:5 |
| 2. | alpha-cypermethrin | 125:1 to 1:125 | 25:1 to 1:25 | 5:1 to 1:5 |
| 3. | betacyfluthrin | 125:1 to 1:125 | 25:1 to 1:25 | 5:1 to 1:5 |
| 4. | cyhalothrin | 125:1 to 1:125 | 25:1 to 1:25 | 5:1 to 1:5 |
| 5. | cypermethrin | 125:1 to 1:125 | 25:1 to 1:25 | 5:1 to 1:5 |
| 6. | deltamethrin | 125:1 to 1:125 | 25:1 to 1:25 | 5:1 to 1:5 |
| 7. | esfenvalerate | 125:1 to 1:125 | 25:1 to 1:25 | 5:1 to 1:5 |
| 8. | etofenprox | 125:1 to 1:125 | 25:1 to 1:25 | 5:1 to 1:5 |
| 9. | fenpropathrin | 125:1 to 1:125 | 25:1 to 1:25 | 5:1 to 1:5 |
| 10. | fenvalerate | 125:1 to 1:125 | 25:1 to 1:25 | 5:1 to 1:5 |
| 11. | flucythrinate | 125:1 to 1:125 | 25:1 to 1:25 | 5:1 to 1:5 |
| 12.a | lambda-cyhalothrin | 125:1 to 1:125 | 25:1 to 1:25 | 5:1 to 1:5 |
| 12.b | gamma-cyhalothrin | 125:1 to 1:125 | 25:1 to 1:25 | 5:1 to 1:5 |
| 13. | permethrin | 125:1 to 1:125 | 25:1 to 1:25 | 5:1 to 1:5 |
| 14. | tau-fluvalinate | 125:1 to 1:125 | 25:1 to 1:25 | 5:1 to 1:5 |
| 15. | transfluthrin | 125:1 to 1:125 | 25:1 to 1:25 | 5:1 to 1:5 |
| 16. | zeta-cypermethrin | 125:1 to 1:125 | 25:1 to 1:25 | 5:1 to 1:5 |
| 17. | cyfluthrin | 125:1 to 1:125 | 25:1 to 1:25 | 5:1 to 1:5 |
| 18. | bifenthrin | 125:1 to 1:125 | 25:1 to 1:25 | 5:1 to 1:5 |
| 19. | tefluthrin | 125:1 to 1:125 | 25:1 to 1:25 | 5:1 to 1:5 |
| 20. | eflusilanate | 125:1 to 1:125 | 25:1 to 1:25 | 5:1 to 1:5 |
| 21. | fubfenprox | 125:1 to 1:125 | 25:1 to 1:25 | 5:1 to 1:5 |
| 22. | pyrethrin | 125:1 to 1:125 | 25:1 to 1:25 | 5:1 to 1:5 |
| 23. | resmethrin | 125:1 to 1:125 | 25:1 to 1:25 | 5:1 to 1:5 |
| 24. | imidacloprid | 125:1 to 1:125 | 25:1 to 1:25 | 5:1 to 1:5 |
| 25. | acetamiprid | 125:1 to 1:125 | 25:1 to 1:25 | 5:1 to 1:5 |
| 26. | thiamethoxam | 125:1 to 1:125 | 25:1 to 1:25 | 5:1 to 1:5 |
| 27. | nitenpyram | 125:1 to 1:125 | 25:1 to 1:25 | 5:1 to 1:5 |
| 28. | thiacloprid | 125:1 to 1:125 | 25:1 to 1:25 | 5:1 to 1:5 |
| 29. | dinotefuran | 125:1 to 1:125 | 25:1 to 1:25 | 5:1 to 1:5 |

-continued

| | Mixing partner | Preferred mixing ratio | More preferred mixing ratio | Most preferred mixing ratio |
|---|---|---|---|---|
| 30. | clothianidin | 125:1 to 1:125 | 25:1 to 1:25 | 5:1 to 1:5 |
| 31. | imidaclothiz | 125:1 to 1:125 | 25:1 to 1:25 | 5:1 to 1:5 |
| 32. | chlorfluazuron | 125:1 to 1:125 | 25:1 to 1:25 | 5:1 to 1:5 |
| 33. | diflubenzuron | 125:1 to 1:125 | 25:1 to 1:25 | 5:1 to 1:5 |
| 34. | lufenuron | 125:1 to 1:125 | 25:1 to 1:25 | 5:1 to 1:5 |
| 35. | teflubenzuron | 125:1 to 1:125 | 25:1 to 1:25 | 5:1 to 1:5 |
| 36. | triflumuron | 125:1 to 1:125 | 25:1 to 1:25 | 5:1 to 1:5 |
| 37. | novaluron | 125:1 to 1:125 | 25:1 to 1:25 | 5:1 to 1:5 |
| 38. | flufenoxuron | 125:1 to 1:125 | 25:1 to 1:25 | 5:1 to 1:5 |
| 39. | hexaflumuron | 125:1 to 1:125 | 25:1 to 1:25 | 5:1 to 1:5 |
| 40. | bistrifluoron | 125:1 to 1:125 | 25:1 to 1:25 | 5:1 to 1:5 |
| 41. | noviflumuron | 125:1 to 1:125 | 25:1 to 1:25 | 5:1 to 1:5 |
| 42. | buprofezin | 625:1 to 1:625 | 125:1 to 1:125 | 25:1 to 1:25 |
| 43. | cyromazine | 125:1 to 1:125 | 25:1 to 1:25 | 5:1 to 1:5 |
| 44. | methoxyfenozide | 125:1 to 1:125 | 25:1 to 1:25 | 5:1 to 1:5 |
| 45. | tebufenozide | 125:1 to 1:125 | 25:1 to 1:25 | 5:1 to 1:5 |
| 46. | halofenozide | 125:1 to 1:125 | 25:1 to 1:25 | 5:1 to 1:5 |
| 48. | chromafenozide | 125:1 to 1:125 | 25:1 to 1:25 | 5:1 to 1:5 |
| 49. | endosulfan | 125:1 to 1:125 | 25:1 to 1:25 | 5:1 to 1:5 |
| 50. | fipronil | 125:1 to 1:125 | 25:1 to 1:25 | 5:1 to 1:5 |
| 51. | ethiprole | 125:1 to 1:125 | 25:1 to 1:25 | 5:1 to 1:5 |
| 52. | pyrafluprole | 125:1 to 1:125 | 25:1 to 1:25 | 5:1 to 1:5 |
| 53. | pyriprole | 125:1 to 1:125 | 25:1 to 1:25 | 5:1 to 1:5 |
| 54. | flubendiamide | 125:1 to 1:125 | 25:1 to 1:25 | 5:1 to 1:5 |
| 55. | chlorantraniliprole (Rynaxypyr) | 125:1 to 1:125 | 25:1 to 1:25 | 5:1 to 1:5 |
| 56. | cyazypyr | 125:1 to 1:125 | 25:1 to 1:25 | 5:1 to 1:5 |
| 57. | emamectin | 125:1 to 1:125 | 25:1 to 1:25 | 5:1 to 1:5 |
| 58. | emamectin benzoate | 125:1 to 1:125 | 25:1 to 1:25 | 5:1 to 1:5 |
| 59. | abamectin | 125:1 to 1:125 | 25:1 to 1:25 | 5:1 to 1:5 |
| 60. | ivermectin | 125:1 to 1:125 | 25:1 to 1:25 | 5:1 to 1:5 |
| 61. | milbemectin | 125:1 to 1:125 | 25:1 to 1:25 | 5:1 to 1:5 |
| 62. | lepimectin | 125:1 to 1:125 | 25:1 to 1:25 | 5:1 to 1:5 |
| 63. | tebufenpyrad | 125:1 to 1:125 | 25:1 to 1:25 | 5:1 to 1:5 |
| 64. | fenpyroximate | 125:1 to 1:125 | 25:1 to 1:25 | 5:1 to 1:5 |
| 65. | pyridaben | 125:1 to 1:125 | 25:1 to 1:25 | 5:1 to 1:5 |
| 66. | fenazaquin | 125:1 to 1:125 | 25:1 to 1:25 | 5:1 to 1:5 |
| 67. | pyrimidifen | 125:1 to 1:125 | 25:1 to 1:25 | 5:1 to 1:5 |
| 68. | tolfenpyrad | 125:1 to 1:125 | 25:1 to 1:25 | 5:1 to 1:5 |
| 69. | dicofol | 125:1 to 1:125 | 25:1 to 1:25 | 5:1 to 1:5 |
| 70. | cyenopyrafen | 125:1 to 1:125 | 25:1 to 1:25 | 5:1 to 1:5 |
| 71. | cyflumetofen | 125:1 to 1:125 | 25:1 to 1:25 | 5:1 to 1:5 |
| 72. | acequinocyl | 125:1 to 1:125 | 25:1 to 1:25 | 5:1 to 1:5 |
| 73. | fluacrypyrin | 125:1 to 1:125 | 25:1 to 1:25 | 5:1 to 1:5 |
| 74. | bifenazate | 125:1 to 1:125 | 25:1 to 1:25 | 5:1 to 1:5 |
| 75. | diafenthiuron | 125:1 to 1:125 | 25:1 to 1:25 | 5:1 to 1:5 |
| 76. | etoxazole | 125:1 to 1:125 | 25:1 to 1:25 | 5:1 to 1:5 |
| 77. | clofentezine | 125:1 to 1:125 | 25:1 to 1:25 | 5:1 to 1:5 |
| 78. | spinosad | 125:1 to 1:125 | 25:1 to 1:25 | 5:1 to 1:5 |
| 79. | triarathen | 125:1 to 1:125 | 25:1 to 1:25 | 5:1 to 1:5 |
| 80. | tetradifon | 125:1 to 1:125 | 25:1 to 1:25 | 5:1 to 1:5 |
| 81. | propargite | 125:1 to 1:125 | 25:1 to 1:25 | 5:1 to 1:5 |
| 82. | hexythiazox | 125:1 to 1:125 | 25:1 to 1:25 | 5:1 to 1:5 |
| 83. | bromopropylate | 125:1 to 1:125 | 25:1 to 1:25 | 5:1 to 1:5 |
| 84. | chinomethionat | 125:1 to 1:125 | 25:1 to 1:25 | 5:1 to 1:5 |
| 85. | amitraz | 125:1 to 1:125 | 25:1 to 1:25 | 5:1 to 1:5 |
| 86. | pyrifluquinazone | 125:1 to 1:125 | 25:1 to 1:25 | 5:1 to 1:5 |
| 87. | pymetrozine | 125:1 to 1:125 | 25:1 to 1:25 | 5:1 to 1:5 |
| 88. | flonicamid | 125:1 to 1:125 | 25:1 to 1:25 | 5:1 to 1:5 |
| 89. | pyriproxyfen | 125:1 to 1:125 | 25:1 to 1:25 | 5:1 to 1:5 |
| 90. | diofenolan | 125:1 to 1:125 | 25:1 to 1:25 | 5:1 to 1:5 |
| 91. | chlorfenapyr | 125:1 to 1:125 | 25:1 to 1:25 | 5:1 to 1:5 |
| 92. | metaflumizone | 125:1 to 1:125 | 25:1 to 1:25 | 5:1 to 1:5 |
| 93. | indoxacarb | 125:1 to 1:125 | 25:1 to 1:25 | 5:1 to 1:5 |
| 94. | chlorpyrifos | 125:1 to 1:125 | 25:1 to 1:25 | 5:1 to 1:5 |
| 95. | spirodiclofen | 125:1 to 1:125 | 25:1 to 1:25 | 5:1 to 1:5 |
| 96. | spiromesifen | 125:1 to 1:125 | 25:1 to 1:25 | 5:1 to 1:5 |
| 97. | spirotetramat | 125:1 to 1:125 | 25:1 to 1:25 | 5:1 to 1:5 |
| 98. | pyridalyl | 125:1 to 1:125 | 25:1 to 1:25 | 5:1 to 1:5 |
| 99. | spinetoram | 125:1 to 1:125 | 25:1 to 1:25 | 5:1 to 1:5 |
| 100. | acephate | 125:1 to 1:125 | 25:1 to 1:25 | 5:1 to 1:5 |
| 101. | triazophos | 125:1 to 1:125 | 25:1 to 1:25 | 5:1 to 1:5 |
| 102. | profenofos | 125:1 to 1:125 | 25:1 to 1:25 | 5:1 to 1:5 |
| 103. | fenamiphos | 125:1 to 1:125 | 25:1 to 1:25 | 5:1 to 1:5 |

-continued

| | Mixing partner | Preferred mixing ratio | More preferred mixing ratio | Most preferred mixing ratio |
|---|---|---|---|---|
| 104. | 4-{[(6-chloropyrid-3-yl)methyl](2,2-difluoro-ethyl)amino}-furan-2(5H)-one | 125:1 to 1:125 | 25:1 to 1:25 | 5:1 to 1:5 |
| 105. | cadusaphos | 125:1 to 1:125 | 25:1 to 1:25 | 5:1 to 1:5 |
| 106. | carbaryl | 125:1 to 1:125 | 25:1 to 1:25 | 5:1 to 1:5 |
| 107. | carbofuran | 125:1 to 1:125 | 25:1 to 1:25 | 5:1 to 1:5 |
| 108. | ethoprophos | 125:1 to 1:125 | 25:1 to 1:25 | 5:1 to 1:5 |
| 109. | thiodicarb | 125:1 to 1:125 | 25:1 to 1:25 | 5:1 to 1:5 |
| 110. | aldicarb | 125:1 to 1:125 | 25:1 to 1:25 | 5:1 to 1:5 |
| 111. | metamidophos | 125:1 to 1:125 | 25:1 to 1:25 | 5:1 to 1:5 |
| 112. | methiocarb | 125:1 to 1:125 | 25:1 to 1:25 | 5:1 to 1:5 |
| 113. | sulfoxaflor | 125:1 to 1:125 | 25:1 to 1:25 | 5:1 to 1:5 |
| 114. | imicyafos | 125:1 to 1:125 | 25:1 to 1:25 | 5:1 to 1:5 |
| 115. | fluensulfone | 125:1 to 1:125 | 25:1 to 1:25 | 5:1 to 1:5 |
| 116. | Bacillus firmus I-1582 | 500:1 to 1:500 | 125:1 to 1:125 | 25:1 to 1:25 |
| 117. | 11-(4-chloro-2,6-dimethylphenyl)-12-hydroxy-1,4-dioxa-9-azadispiro[4.2.4.2]tetra dec-11-en-10-one | 125:1 to 1:125 | 25:1 to 1:25 | 5:1 to 1:5 |
| 118. | 2-{6-[2-(5-fluoropyridin-3-yl)-1,3-thiazol-5-yl]pyridin-2-yl}pyrimidine | 125:1 to 1:125 | 25:1 to 1:25 | 5:1 to 1:5 |

The inventive active ingredient combinations, given good plant tolerance, favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development. The abovementioned pests include: From the order of the Anoplura (*Phthiraptera*), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus mactans, Metatetranychus* spp., *Nuphersa* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acalymma vittatum, Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Psylliodes* spp., *Ptinus* spp., *Rhizobius ventralis, Rhizopertha dominica, Sitophilus* spp., *Sphenophorus* spp., *Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Diplopoda, for example, *Blaniulus guttulatus.*

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Cochliomyia* spp., *Contarinia* spp., *Cordylobia anthropophaga, Culex* spp., *Cuterebra* spp., *Dacus oleae, Dasyneura* spp., *Delia* spp., *Dermatobia hominis, Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit, Pegomyia* spp., *Phorbia* spp., *Prodiplosis* spp., *Psila rosae, Rhagoletis* spp., *Stomoxys* spp., *Tabanus* spp., *Tannia* spp., *Tetanops* spp., *Tipula* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., Loa Loa, *Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is also possible to control protozoa, such as Eimeria.

From the order of the Heteroptera, for example, *Anasa tristis, Antestiopsis* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the *Homoptera*, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the *Hymenoptera*, for example, *Athalia* spp., *Diprion* spp., *Hoplocampa* spp., *Lasius* spp., *Monomorium pharaonis, Vespa* spp.

From the order of the Isopoda, for example, *Armadillidium vulgare, Oniscus asellus* and *Porcellio scaber.*

From the order of the *Isoptera*, for example, *Acromyrmex* spp., *Atta* spp., *Cornitermes cumulans, Microtermes obesi, Odontotermes* spp., *Reticulitermes* spp.

From the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana* saccharina, *Ephestia kuehniella, Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichoplusia* spp., *Tuta absoluta, Virachola* spp.

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloid-*

*ogyne* spp., *Pratylenchus* spp., *Radopholus similis, Trichodorus* spp., *Tylenchulus semipenetrans, Xiphinema* spp.

The active ingredient combinations can be converted to the customary formulations, such as solutions, emulsions, wettable powders, suspensions, powders, dusts, pastes, soluble powders, granules, suspoemulsion concentrates, natural products impregnated with active ingredient, synthetic substances impregnated with active ingredient, and also microencapsulations in polymeric substances.

These formulations are produced in a known manner, for example by mixing the active ingredients with extenders, i.e. liquid solvents, and/or solid carriers, optionally with the use of surfactants, i.e. emulsifiers and/or dispersants, and/or foam formers.

If the extender used is water, it is also possible to use, for example, organic solvents as auxiliary solvents. Useful liquid solvents essentially include: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

Useful solid carriers include:

for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are for example lignosulphite waste liquors and methylcellulose.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

The formulations contain generally between 0.1 and 95% by weight of active ingredient, preferably between 0.5 and 90%.

The inventive active ingredient combinations may be present in commercially available formulations and in the use forms, prepared from these formulations, as a mixture with other active ingredients, such as insecticides, attractants, sterilants, bactericides, acaricides, nematicides, fungicides, growth regulators or herbicides. The insecticides include, for example, phosphoric esters, carbamates, carboxylic esters, chlorinated hydrocarbons, phenylureas, substances produced by microorganisms, etc.

A mixture with other known active ingredients, such as herbicides, or with fertilizers and growth regulators, is also possible.

When used as insecticides, the inventive active ingredient combinations may also be present in their commercially available formulations and in the use forms, prepared from these formulations, as a mixture with synergists. Synergists are compounds which enhance the action of the active ingredients, without any need for the synergist added to be active itself.

The active ingredient content of the use forms prepared from the commercially available formulations may vary within wide limits. The active ingredient concentration of the application forms may be from 0.0000001 to 95% by weight of active ingredient, preferably between 0.0001 and 1% by weight.

The compounds are applied in a customary manner appropriate for the use forms.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant varieties which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits, seeds, roots, tubers and rhizomes. The plant parts also include harvested material and vegetative and generative propagation material, for example cuttings, tubers, rhizomes, slips and seeds.

The inventive treatment of the plants and plant parts with the active ingredient combinations is effected directly or by allowing them to act on the surroundings, habitat or storage space thereof by the customary treatment methods, for example by dipping, spraying, vaporizing, pouring on, nebulizing, scattering, painting on, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetical engineering, if appropriate in combination with conventional methods (Genetically Modified Organisms), and parts thereof are treated. The term "parts" or "parts of plants" or "plant parts" has been explained above.

More preferably, plants of the plant cultivars which are each commercially available or in use are treated in accordance with the invention.

Depending on the plant species or plant cultivars, and the location and growth conditions (soils, climate, vegetation period, diet) thereof, the inventive treatment may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, increased storage life and/or processibility of the harvested products, which exceed the effects normally to be expected.

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active ingredients. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA (b), CryIA(c), CryIIA, CryIIIA, CryIIIB2, Cry9c Cry2Ab, Cry3Bb and CryIF and also combinations thereof) (hereinbelow referred to as "Bt plants"). Traits that are additionally particularly emphasized are the increased tolerance of the plants to certain active herbicidal ingredients, for example imidazolinones, sulphonylureas, glyphosate or phosphinothricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicide-tolerant plants include maize varieties, cotton varieties and soya varieties which are sold under the trade names Roundup Ready® (tolerance to glyphosate, for example maize, cotton, soya), Liberty Link® (tolerance to phosphinothricin, for example oilseed rape), IMF® (tolerance to imidazolinones) and STS® (tolerance to sulphonylureas, for example maize). Herbicide-resistant plants (plants bred in a conventional manner for herbicide tolerance) also include the varieties sold under the Clearfield® name (for example maize). Of course, these statements also apply to plant cultivars which have these genetic traits or genetic traits which are still to be developed and will be developed and/or marketed in the future.

The plants listed can be treated according to the invention in a particularly advantageous manner with the active compound mixture according to the invention. The preferred ranges stated above for the mixtures also apply to the treatment of these plants. Particular emphasis is given to the treatment of plants with the mixtures specifically mentioned in the present text.

The good insecticidal and acaricidal action of the inventive active ingredient combinations is evident from the examples which follow. While the individual active ingredients have weaknesses in their action, the combinations exhibit an action which exceeds a simple sum of actions.

A synergistic effect in insecticides and acaricides is present whenever the action of the active ingredient combinations is greater than the sum of the actions of the active ingredients applied individually.

Use Examples

The expected action for a given combination of two active ingredients can be calculated according to S. R. Colby, Weeds 15 (1967), 20-22 as follows:

If

X is the kill rate, expressed in % of the untreated control, in the case of use of active ingredient A in an application rate of $\underline{m}$ g/ha or in a concentration of $\underline{m}$ ppm, Y is the kill rate, expressed in % of the untreated control, in the case of use of active ingredient B in an application rate of $\underline{n}$ g/ha or in a concentration of $\underline{n}$ ppm, and E is the kill rate, expressed in % of the untreated control, in the case of use of active ingredients A and B in application rates of $\underline{m}$ and $\underline{n}$ g/ha or in a concentration of $\underline{m}$ and $\underline{n}$ ppm, then $$E = X + Y - \frac{X \cdot Y}{100}.$$

If the actual kill rate is greater than that calculated, the kill rate of the combination is superadditive, which means that a synergistic effect is present. In this case, the kill rate actually observed must be greater than the value calculated from the above formula for the expected kill rate (E).

Example A

*Myzus Persicae* Test

Solvent: 78 parts by weight of acetone 1.5 parts by weight of dimethylformamide

Emulsifier: 0.5 part by weight of alkylaryl polyglycol ether

To produce an appropriate active ingredient formulation, 1 part by weight of active ingredient is mixed with the stated amounts of solvent and emulsifier, and the concentrate is diluted with emulsifier-containing water to the desired concentration.

Cabbage leaves (*Brassica oleracea*) severely infested by the green peach aphid (*Myzus persicae*) are treated by spraying with the active ingredient formulation in the desired concentration.

After the desired time, the kill in % is determined 100% means that all aphids have been killed; 0% means that no aphids have been killed. The kill rates determined are entered into Colby's formula.

In this test, the following active ingredient combinations according to the present invention, for example, exhibited a synergistic enhancement in activity compared to the active ingredients applied individually:

TABLE A

*Myzus persicae* test

| Active ingredient | Concentration in g/ha | Kill rate in % after $1^d$ found* | calc.** |
|---|---|---|---|
| compound (I-1-2)/ compound (I-1-8)*** | 4 | 0 | |
| | 0.8 | 0 | |
| | 0.16 | 0 | |
| | 0.032 | 0 | |
| compound (I-1-1)/ compound (I-1-7)*** | 4 | 80 | |
| | 0.8 | 0 | |
| | 0.16 | 0 | |
| | 0.032 | 0 | |
| abamectin | 0.16 | 0 | |
| | | found* | calc.** |
| compound (I-1-1)/compound (I-1-7)*** + abamectin (5:1) inventive | 0.8 + 0.16 | 70 | 0 |
| acephate | 100 | 0 | |
| | | found* | calc.** |
| compound (I-1-2)/compound (I-1-8)*** + acephate (1:25) inventive | 4 + 100 | 80 | 0 |
| acrinathrin | 0.8 | 0 | |
| | | found* | calc.** |
| compound (I-1-2)/compound (I-1-8)*** + acrinathrin (1:25) inventive | 0.032 + 0.8 | 90 | 0 |
| compound (I-1-1)/compound (I-1-7)*** + acrinathrin (1:25) inventive | 0.032 + 0.8 | 80 | 0 |
| alpha-cypermethrin | 0.16 | 70 | |
| | | found* | calc.** |
| compound (I-1-2)/compound (I-1-8)*** + alpha-cypermethrin (1:1) inventive | 0.16 + 0.16 | 90 | 70 |
| *Bacillus firmus* strain I-1582 | 250 | 0 | |
| | | found* | calc.** |
| compound (I-1-1)/compound (I-1-7)*** + *Bacillus firmus* I-1582 (1:312.5) inventive | 0.8 + 250 | 100 | 80 |
| bifenthrin | 0.8 | 80 | |
| | | found* | calc.** |
| compound (I-1-1)/compound (I-1-7)*** + bifenthrin (1:1) inventive | 0.8 + 0.8 | 100 | 80 |
| β-cyfluthrin | 0.16 | 70 | |
| | 0.032 | 0 | |
| | | found* | calc.** |
| compound (I-1-2)/compound (I-1-8)*** + β-cyfluthrin (5:1) inventive | 0.16 + 0.032 | 70 | 0 |
| compound (I-1-1)/compound (I-1-7)*** + β-cyfluthrin (5:1) inventive | 0.8 + 0.16 | 90 | 70 |
| buprofezin | 500 | 0 | |
| | | found* | calc.** |
| compound (I-1-1)/compound (I-1-7)*** + buprofezin (1:625) inventive | 0.8 + 500 | 70 | 0 |
| cadusaphos | 20 | 0 | |
| | | found* | calc.** |
| compound (I-1-2)/compound (I-1-8)*** + cadusaphos (1:25) inventive | 0.8 + 20 | 90 | 0 |

TABLE A-continued

*Myzus persicae* test

| Active ingredient | Concentration in g/ha | | |
|---|---|---|---|
| compound (I-1-1)/compound (I-1-7)*** + cadusaphos (1:25) inventive | 0.8 + 20 | 90 | 0 |
| carbaryl | 500 | 0 | |
| | | found* | calc.** |
| compound (I-1-2)/compound (I-1-8)*** + carbaryl (1:125) inventive | 4 + 500 | 90 | 0 |
| carbofuran | 20 | 70 | |
| | | found* | calc.** |
| compound (I-1-2)/compound (I-1-8)*** + carbofuran (1:25) inventive | 0.8 + 20 | 90 | 70 |
| chlorpyrifos | 4 | 80 | |
| | | found* | calc.** |
| compound (I-1-2)/compound (I-1-8)*** + chlorpyrifos (1:25) inventive | 0.16 + 4 | 100 | 80 |
| clothianidin | 20 | 70 | |
| | | found* | calc.** |
| compound (I-1-2)/compound (I-1-8)*** + clothianidin (1:5) inventive | 4 + 20 | 90 | 70 |
| cypermethrin | 4 | 80 | |
| | | found* | calc.** |
| compound (I-1-1)/compound (I-1-7)*** + cypermethrin (1:5) inventive | 0.8 + 4 | 100 | 80 |
| deltamethrin | 0.8 | 0 | |
| | | found* | calc.** |
| compound (I-1-2)/compound (I-1-8)*** + deltamethrin (1:1) inventive | 0.8 + 0.8 | 100 | 0 |
| compound (I-1-1)/compound (I-1-7)*** + deltamethrin (1:1) inventive | 0.8 + 0.8 | 80 | 0 |
| diafenthiuron | 100 | 0 | |
| | | found* | calc.** |
| compound (I-1-1)/compound (I-1-7)*** + diafenthiuron (1:125) inventive | 0.8 + 100 | 70 | 0 |
| emamectin benzoate | 0.8 | 0 | |
| | 0.16 | 0 | |
| | | found* | calc.** |
| compound (I-1-2)/compound (I-1-8)*** + emamectin benzoate (5:1) inventive | 4 + 0.8 | 70 | 0 |
| compound (I-1-1)/compound (I-1-7)*** + emamectin benzoate (5:1) inventive | 0.8 + 0.16 | 70 | 0 |
| ethiprole | 4 | 0 | |
| | | found* | calc.** |
| compound (I-1-2)/compound (I-1-8)*** + ethiprole (1:5) inventive | 0.8 + 4 | 80 | 0 |
| compound (I-1-1)/compound (I-1-7)*** + ethiprole (1:5) inventive | 0.8 + 4 | 70 | 0 |
| flonicamid | 20 | 0 | |
| | | found* | calc.** |
| compound (I-1-2)/compound (I-1-8)*** + flonicamid (1:25) inventive | 0.8 + 20 | 80 | 0 |

TABLE A-continued

*Myzus persicae* test

| Active ingredient | Concentration in g/ha | | found* | calc.** |
|---|---|---|---|---|
| compound (I-1-1)/compound (I-1-7)*** + flonicamid (1:25) inventive | 0.8 + 20 | | 70 | 0 |
| gamma-cyhalothrin | 0.032 | 0 | | |
| | | | found* | calc.** |
| compound (I-1-1)/compound (I-1-7)*** + gamma-cyhalothrin (5:1) inventive | 0.16 + 0.032 | | 70 | 0 |
| imidacloprid | 0.8 | 0 | | |
| | | | found* | calc.** |
| compound (I-1-2)/compound (I-1-8)*** + imidacloprid (1:25) inventive | 0.032 + 0.8 | | 70 | 0 |
| compound (I-1-1)/compound (I-1-7)*** + imidacloprid (1:25) inventive | 0.032 + 0.8 | | 70 | 0 |
| indoxacarb | 20 | 0 | | |
| | | | found* | calc.** |
| compound (I-1-2)/compound (I-1-8)*** + indoxacarb (1:25) inventive | 0.8 + 20 | | 70 | 0 |
| compound (I-1-1)/compound (I-1-7)*** + indoxacarb (1:25) inventive | 0.8 + 20 | | 80 | 0 |
| L-cyhalothrin | 0.16 | 0 | | |
| | | | found* | calc.** |
| compound (I-1-2)/compound (I-1-8)*** + L-cyhalothrin (1:1) inventive | 0.16 + 0.16 | | 80 | 0 |
| compound (I-1-1)/compound (I-1-7)*** + L-cyhalothrin (1:1) inventive | 0.16 + 0.16 | | 90 | 0 |
| metaflumizone | 20 | 0 | | |
| | | | found* | calc.** |
| compound (I-1-2)/compound (I-1-8)*** + metaflumizone (1:25) inventive | 0.8 + 20 | | 70 | 0 |
| compound (I-1-1)/compound (I-1-7)*** + metaflumizone (1:25) inventive | 0.8 + 20 | | 70 | 0 |
| methamidophos | 100<br>20 | 80<br>0 | | |
| | | | found* | calc.** |
| compound (I-1-2)/ compound (I-1-8)*** + methamidophos (1:25) inventive | 4 + 100 | | 100 | 80 |
| compound (I-1-1)/ compound (I-1-7)*** + methamidophos (1:25) inventive | 0.8 + 20 | | 90 | 0 |
| methiocarb | 20 | 0 | | |
| | | | found* | calc.** |
| compound (I-1-2)/compound (I-1-8)*** + methiocarb (1:25) inventive | 0.8 + 20 | | 70 | 0 |
| compound (I-1-1)/compound (I-1-7)*** + methiocarb (1:25) inventive | 0.8 + 20 | | 70 | 0 |
| milbemectin | 0.8 | 0 | | |

TABLE A-continued

*Myzus persicae* test

| Active ingredient | Concentration in g/ha | | found* | calc.** |
|---|---|---|---|---|
| compound (I-1-1)/compound (I-1-7)*** + milbemectin (1:1) inventive | 0.8 + 0.8 | | 70 | 0 |
| pyridalyl | 4 | 0 | | |
| | | | found* | calc.** |
| compound (I-1-2)/compound (I-1-8)*** + pyridalyl (1:5) inventive | 0.8 + 4 | | 70 | 0 |
| spinetoram | 4 | 0 | | |
| | | | found* | calc.** |
| compound (I-1-2)/compound (I-1-8)*** + spinetoram (1:1) inventive | 4 + 4 | | 70 | 0 |
| spirodiclofen | 100<br>20 | 0<br>0 | | |
| | | | found* | calc.** |
| compound (I-1-2)/compound (I-1-8)*** + spirodiclofen (1:25) inventive | 4 + 100 | | 70 | 0 |
| compound (I-1-1)/compound (I-1-7)*** + spirodiclofen (1:25) inventive | 0.8 + 20 | | 70 | 0 |
| spiromesifen | 4 | 0 | | |
| | | | found* | calc.** |
| compound (I-1-1)/compound (I-1-7)*** + spiromesifen (1:5) inventive | 0.8 + 4 | | 70 | 0 |
| sulfoxaflor | 0.16 | 0 | | |
| | | | found* | calc.** |
| compound (I-1-1)/compound (I-1-7)*** + sulfoxaflor (1:1) inventive | 0.16 + 0.16 | | 70 | 0 |
| tebufenpyrad | 0.8 | 0 | | |
| | | | found* | calc.** |
| compound (I-1-1)/compound (I-1-7)*** + tebufenpyrad (1:1) inventive | 0.8 + 0.8 | | 70 | 0 |
| thiacloprid | 20 | 80 | | |
| | | | found* | calc.** |
| compound (I-1-2)/compound (I-1-8)*** + thiacloprid (1:5) inventive | 4 + 20 | | 100 | 80 |
| thiamethoxam | 20 | 70 | | |
| | | | found* | calc.** |
| compound (I-1-2)/compound (I-1-8)*** + thiamethoxam (1:5) inventive | 4 + 20 | | 100 | 70 |
| compound (I-1-1)/compound (I-1-7)*** + thiamethoxam (1:5) inventive | 0.8 + 4 | | 90 | 70 |
| thiodicarb | 20 | 0 | | |
| | | | found* | calc.** |
| compound (I-1-2)/compound (I-1-8)*** + thiodicarb (1:25) inventive | 0.8 + 20 | | 70 | 0 |
| compound (I-1-1)/compound (I-1-7)*** + thiodicarb (1:25) inventive | 0.8 + 20 | | 70 | 0 |
| transfluthrin | 20 | 70 | | |

TABLE A-continued

| *Myzus persicae* test | | | |
|---|---|---|---|
| Active ingredient | Concentration in g/ha | | |
| | | found* | calc.** |
| compound (I-1-2)/compound (I-1-8)*** + transfluthrin (1:25) inventive | 0.8 + 20 | 90 | 70 |
| triazophos | 100 | 0 | |
| | | found* | calc.** |
| compound (I-1-2)/compound (I-1-8)*** + triazophos (1:125) inventive | 0.8 + 100 | 70 | 0 |
| compound (I-1-1)/compound (I-1-7)*** + triazophos (1:125) inventive | 0.8 + 100 | 70 | 0 |
| 4-{[(6-CHLOROPYRID-3-YL)METHYL](2,2-DIFLUOROETHYL)AMINO}FURAN-2(5H)-ONE | 20 | 0 | |
| | | found* | calc.** |
| compound (I-1-1)/compound (I-1-7)*** + 4-{[(6-CHLOROPYRID-3-YL)METHYL](2,2-DIFLUOROETHYL)AMINO}FURAN-2(5H)-ONE (125:1) inventive | 20 + 0.16 | 70 | 0 |
| pymetrozine | 100 | 0 | |
| | | found* | calc.** |
| compound (I-1-1)/compound (I-1-7)*** + pymetrozine (1:25) inventive | 4 + 100 | 100 | 0 |
| cyromazine | 100 | 0 | |
| | | found* | calc.** |
| compound (I-1-1)/compound (I-1-7)*** + cyromazine (1:25) inventive | 4 + 100 | 70 | 0 |
| | | Kill rate in % after $6^d$ | |
| compound (I-1-2)/compound (I-1-8)*** | 0.16<br>0.032 | 0<br>0 | |
| compound (I-1-1)/compound (I-1-7)*** | 0.16<br>0.032 | 70<br>0 | |
| acetamiprid | 0.16 | 0 | |
| | | found* | calc.** |
| compound (I-1-1)/compound (I-1-7)*** + acetamiprid (1:5) inventive | 0.032 + 0.16 | 70 | 0 |
| aldicarb | 0.8 | 0 | |
| | | found* | calc.** |
| compound (I-1-2)/compound (I-1-8)*** + aldicarb (1:5) inventive | 0.16 + 0.8 | 80 | 0 |
| chlorfenapyr | 0.8<br>0.16 | 0<br>0 | |
| | | found* | calc.** |
| compound (I-1-2)/compound (I-1-8)*** + chlorfenapyr (1:5) inventive | 0.16 + 0.8 | 80 | 0 |
| compound (I-1-1)/compound (I-1-7)*** + chlorfenapyr (1:5) inventive | 0.032 + 0.16 | 70 | 0 |
| clothianidin | 0.16 | 0 | |
| | | found* | calc.** |
| compound (I-1-1)/compound (I-1-7)*** + clothianidin (1:5) inventive | 0.032 + 0.16 | 70 | 0 |
| cyantraniliprole | 0.16 | 0 | |

TABLE A-continued

| *Myzus persicae* test | | | |
|---|---|---|---|
| Active ingredient | Concentration in g/ha | | |
| | | found* | calc.** |
| compound (I-1-2)/compound (I-1-8)*** + cyantraniliprole (1:5) inventive | 0.032 + 0.16 | 80 | 0 |
| compound (I-1-1)/compound (I-1-7)*** + cyantraniliprole (1:5) inventive | 0.032 + 0.16 | 70 | 0 |
| diafenthiuron | 20 | 70 | |
| | | found* | calc.** |
| compound (I-1-2)/compound (I-1-8)*** + diafenthiuron (1:125) inventive | 0.16 + 20 | 100 | 70 |
| ethoprophos | 4 | 0 | |
| | | found* | calc.** |
| compound (I-1-2)/compound (I-1-8)*** + ethoprophos (1:25) inventive | 0.16 + 4 | 80 | 0 |
| fenamiphos | 0.8 | 0 | |
| | | found* | calc.** |
| compound (I-1-1)/compound (I-1-7)*** + fenamiphos (1:25) inventive | 0.032 + 0.8 | 70 | 0 |
| 11-(4-CHLORO-2,6-DIMETHYLPHENYL)-12-HYDROXY-1,4-DIOXA-9-AZADISPIRO[4.2.4.2]TETRADEC-11-EN-10-ONE | 0.8 | 0 | |
| | | found* | calc.** |
| compound (I-1-1)/compound (I-1-7)*** + 11-(4-CHLORO-2,6-DIMETHYLPHENYL)-12-HYDROXY-1,4-DIOXA-9-AZADISPIRO[4.2.4.2]TETRADEC-11-EN-10-ONE (1:25) inventive | 0.032 + 0.8 | 70 | 0 |
| fipronil | 0.16 | 0 | |
| | | found* | calc.** |
| compound (I-1-2)/compound (I-1-8)*** + fipronil (1:1) inventive | 0.16 + 0.16 | 80 | 0 |
| flufenoxuron | 0.8 | 0 | |
| | | found* | calc.** |
| compound (I-1-1)/compound (I-1-7)*** + flufenoxuron (1:25) inventive | 0.032 + 0.8 | 70 | 0 |
| methoxyfenozide | 4 | 0 | |
| | | found* | calc.** |
| compound (I-1-2)/compound (I-1-8)*** + methoxyfenozide (1:25) inventive | 0.16 + 4 | 100 | 0 |
| milbemectin | 0.032 | 0 | |
| | | found* | calc.** |
| compound (I-1-1)/compound (I-1-7)*** + milbemectin (1:1) inventive | 0.032 + 0.032 | 70 | 0 |
| tebufenozide | 4 | 0 | |
| | | found* | calc.** |
| compound (I-1-2)/compound (I-1-8)*** + tebufenozide (1:25) inventive | 0.16 + 4 | 100 | 0 |
| tebufenpyrad | 0.16 | 0 | |

TABLE A-continued

| *Myzus persicae* test | | | |
|---|---|---|---|
| Active ingredient | Concentration in g/ha | | |
| | | found* | calc.** |
| compound (I-1-2)/compound (I-1-8)*** + tebufenpyrad (1:1) inventive | 0.16 + 0.16 | 80 | 0 |
| triflumuron | 20 | 0 | |
| | 4 | 0 | |
| | | found* | calc.** |
| compound (I-1-2)/compound (I-1-8)*** + triflumuron (1:125) inventive | 0.16 + 20 | 90 | 0 |
| compound (I-1-1)/compound (I-1-7)*** + triflumuron (1:125) inventive | 0.032 + 4 | 70 | 0 |
| spinetoram | 0.8 | 0 | |
| | | found* | calc.** |
| compound (I-1-1)/compound (I-1-7)*** + spinetoram (1:5) inventive | 0.16 + 0.8 | 90 | 70 |
| thiacloprid | 0.8 | 80 | |
| | | found* | calc.** |
| compound (I-1-1)/compound (I-1-7)*** + thiacloprid (1:25) inventive | 0.032 + 0.8 | 100 | 80 |
| 2-{6-[2-(5-FLUOROPYRIDIN-3-YL)-1,3-THIAZOL-5-YL]PYRIDIN-2-YL}PYRIMIDINE | 0.8 | 70 | |
| | | found* | calc.** |
| compound (I-1-1)/compound (I-1-7)*** + 2-{6-[2-(5-FLUOROPYRIDIN-3-YL)-1,3-THIAZOL-5-YL]PYRIDIN-2-YL}PYRIMIDINE (1:25) inventive | 0.032 + 0.8 | 100 | 70 |

*found = effect found

**calc. = effect calculated by Colby's formula

***In the tested mixtures of compound (I-1-1)/compound (I-1-7) or compound (I-1-2)/compound (I-1-8), the compounds (I-1-1) and (I-1-2) were each present to an extent of approx. 85% or approx. 84%, and the compounds (I-1-7) and (I-1-8) each to an extent of approx. 15%.

Example B

*Phaedon Cochleariae* Larvae Test

Solvent: 78 parts by weight of acetone 1.5 parts by weight of dimethylformamide

Emulsifier: 0.5 part by weight of alkylaryl polyglycol ether

To produce an appropriate active ingredient formulation, 1 part by weight of active ingredient is mixed with the stated amounts of solvent and emulsifier, and the concentrate is diluted with emulsifier-containing water to the desired concentration.

Cabbage leaves (*Brassica oleracea*) are treated by spraying with the active ingredient formulation of the desired concentration and populated with larvae of the mustard beetle (*Phaedon cochleariae*) while the leaves are still moist.

After the desired period of time, the kill rate in % is determined. 100% means that all beetle larvae have been killed; 0% means that none of the beetle larvae have been killed. The kill rates determined are entered into Colby's formula.

In this test, the following active ingredient combinations according to the present application exhibit a synergistic enhancement in activity compared to the active ingredients applied individually:

TABLE B

| Phaedon *cochleariae larvae* test | | | |
|---|---|---|---|
| Active ingredient | Concentration in g/ha | | |
| | | Kill rate in % after $2^d$ | |
| compound (I-1-2)/compound (I-1-8)*** | 0.16 | 50 | |
| | 0.032 | 0 | |
| compound (I-1-1)/compound (I-1-7)*** | 0.16 | 67 | |
| aldicarb | 0.8 | 0 | |
| | | found* | calc.** |
| compound (I-1-1)/compound (I-1-7)*** + aldicarb (1:5) inventive | 0.16 + 0.8 | 100 | 67 |
| β-cyfluthrin | 0.032 | 0 | |
| | | found* | calc.** |
| compound (I-1-2)/compound (I-1-8)*** + β-cyfluthrin (5:1) inventive | 0.16 + 0.032 | 67 | 50 |
| cyantraniliprole | 0.16 | 0 | |
| | | found* | calc.** |
| compound (I-1-2)/compound (I-1-8)*** + cyantraniliprole (1:5) inventive | 0.032 + 0.16 | 33 | 0 |
| dinotefuran | 20 | 0 | |
| | | found* | calc.** |
| compound (I-1-2)/compound (I-1-8)*** + dinotefuran (1:125) inventive | 0.16 + 20 | 83 | 50 |
| compound (I-1-1)/compound (I-1-7)*** + dinotefuran (1:125) inventive | 0.16 + 20 | 100 | 67 |
| fipronil | 0.16 | 67 | |
| | | found* | calc.** |
| compound (I-1-2)/compound (I-1-8)*** + fipronil (1:1) inventive | 0.16 + 0.16 | 100 | 83.5 |
| | | found* | calc.** |
| compound (I-1-1)/compound (I-1-7)*** + fipronil (1:1) inventive | 0.16 + 0.16 | 100 | 83.5 |
| profenophos | 4 | 0 | |
| | | found* | calc.** |
| compound (I-1-2)/compound (I-1-8)*** + profenophos (1:25) inventive | 0.16 + 4 | 83 | 50 |
| tebufenozide | 4 | 0 | |
| | | found* | calc.** |
| compound (I-1-2)/compound (I-1-8)*** + tebufenozide (1:1) inventive | 0.16 + 4 | 83 | 50 |
| | | Kill rate in % after $6^d$ | |
| compound (I-1-2)/compound (I-1-8)*** | 0.032 | 0 | |
| compound (I-1-1)/compound (I-1-7)*** | 0.16 | 83 | |
| | 0.032 | 0 | |
| abamectin | 0.032 | 0 | |
| | | found* | calc.** |
| compound (I-1-1)/compound (I-1-7)*** + abamectin (5:1) inventive | 0.16 + 0.032 | 100 | 83 |
| acephate | 4 | 0 | |

TABLE B-continued

Phaedon *cochleariae larvae* test

| Active ingredient | Concentration in g/ha | found* | calc.** |
|---|---|---|---|
| compound (I-1-1)/compound (I-1-7)*** + acephate (1:25) inventive | 0.16 + 4 | 100 | 83 |
| cyantraniliprole | 0.16 | 0 | |
| | | found* | calc.** |
| compound (I-1-2)/compound (I-1-8)*** + cyantraniliprole (1:5) inventive | 0.032 + 0.16 | 50 | 0 |
| compound (I-1-1)/compound (I-1-7)*** + cyantraniliprole (1:5) inventive | 0.032 + 0.16 | 100 | 0 |
| cypermethrin | 0.16 | 0 | |
| | | found* | calc.** |
| compound (I-1-2)/compound (I-1-8)*** + cypermethrin (1:5) inventive | 0.032 + 0.16 | 33 | 0 |
| emamectin benzoate | 0.032 | 0 | |
| | | found* | calc.** |
| compound (I-1-1)/compound (I-1-7)*** + emamectin benzoate (5:1) inventive | 0.16 + 0.032 | 100 | 83 |
| ethoprophos | 0.8 | 0 | |
| | | found* | calc.** |
| compound (I-1-2)/compound (I-1-8)*** + ethoprophos (1:25) inventive | 0.032 + 0.8 | 33 | 0 |
| flubendiamide | 0.8 | 0 | |
| | | found* | calc.** |
| compound (I-1-1)/compound (I-1-7)*** + flubendiamide (1:5) inventive | 0.16 + 0.8 | 100 | 83 |
| novaluron | 0.8 | 0 | |
| | | found* | calc.** |
| compound (I-1-1)/compound (I-1-7)*** + novaluron (1:5) inventive | 0.16 + 0.8 | 100 | 83 |
| profenophos | 4 | 0 | |
| | | found* | calc.** |
| compound (I-1-1)/compound (I-1-7)*** + profenophos (1:25) inventive | 0.16 + 4 | 100 | 83 |
| spirodiclofen | 4 | 0 | |
| | | found* | calc.** |
| compound (I-1-1)/compound (I-1-7)*** + spirodiclofen (1:25) inventive | 0.16 + 4 | 100 | 83 |
| tebufenpyrad | 0.16 | 0 | |
| | | found* | calc.** |
| compound (I-1-1)/compound (I-1-7)*** + tebufenpyrad (1:1) inventive | 0.16 + 0.16 | 100 | 83 |
| triflumuron | 4 | 0 | |
| | | found* | calc.** |
| compound (I-1-2)/compound (I-1-8)*** + triflumuron (1:125) inventive | 0.032 + 4 | 50 | 0 |
| spinetoram | 0.16 | 0 | |
| | | found* | calc.** |
| compound (I-1-1)/compound (I-1-7)*** + spinetoram (1:5) inventive | 0.032 + 0.16 | 33 | 0 |
| pyridalyl | 4 | 0 | |
| | | found* | calc.** |
| compound (I-1-1)/compound (I-1-7)*** + pyridalyl (1:25) inventive | 0.16 + 4 | 100 | 83 |
| methoxyfenozide | 0.8 | 0 | |
| | | found* | calc.** |
| compound (I-1-1)/compound (I-1-7)*** + methoxyfenozide (1:5) inventive | 0.16 + 0.8 | 100 | 83 |
| 2-{6-[2-(5-FLUOROPYRIDIN-3-YL)-1,3-THIAZOL-5-YL]PYRIDIN-2-YL}PYRIMIDINE | 0.16 | 0 | |
| | | found* | calc.** |
| compound (I-1-1)/compound (I-1-7)*** + 2-{6-[2-(5-FLUOROPYRIDIN-3-YL)-1,3-THIAZOL-5-YL]PYRIDIN-2-YL}PYRIMIDINE (1:25) inventive | 0.16 + 4 | 100 | 83 |
| cyromazine | 4 | 0 | |
| | | found* | calc.** |
| compound (I-1-1)/compound (I-1-7)*** + cyromazine (1:25) inventive | 0.16 + 4 | 100 | 83 |
| cyflumetofen | 4 | 0 | |
| | | found* | calc.** |
| compound (I-1-1)/compound (I-1-7)*** + Cyflumetofen (1:25) inventive | 0.16 + 4 | 100 | 83 |

*found = effect found

**calc. = effect calculated by Colby's formula

***In the tested mixtures of compound (I-1-1)/compound (I-1-7) or compound (I-1-2)/compound (I-1-8), the compounds (I-1-1) and (I-1-2) were each present to an extent of approx. 85% or approx. 84%, and the compounds (I-1-7) and (I-1-8) each to an extent of approx. 15%.

Example C

*Spodoptera Frugiperda* Larvae Test

Solvent: 78 parts by weight of acetone 1.5 parts by weight of dimethylformamide

Emulsifier: 0.5 part by weight of alkylaryl polyglycol ether

To produce an appropriate active ingredient formulation, 1 part by weight of active ingredient is mixed with the stated amounts of solvent and emulsifier, and the concentrate is diluted with emulsifier-containing water to the desired concentration.

Cabbage leaves (*Brassica oleracea*) are treated by spraying with the active ingredient formulation of the desired concentration and populated with larvae of the army worm (*Spodopter frugiperda*) while the leaves are still moist.

After the desired time, the kill in % is determined 100% means that all caterpillars have been killed; 0% means that none of the caterpillars have been killed. The kill rates determined are entered into Colby's formula.

In this test, the following active ingredient combinations according to the present application exhibit a synergistic enhancement in activity compared to the active ingredients applied individually:

TABLE C

| *Spodoptera frugiperda* larvae test | | | |
|---|---|---|---|
| Active ingredient | Concentration in g/ha | | |
| | | Kill rate in % after 2[d] | |
| compound (I-1-2)/compound (I-1-8)*** | 0.16 | 33 | |
| | 0.032 | 17 | |
| fenpyroximate | 0.8 | 0 | |
| | | found* | calc.** |
| compound (I-1-2)/compound (I-1-8)*** + fenpyroximate (1:5) inventive | 0.16 + 0.8 | 83 | 33 |
| gamma-cyhalothrin | 0.032 | 17 | |
| | | found* | calc.** |
| compound (I-1-2)/compound (I-1-8)*** + fenpyroximate (5:1) inventive | 0.16 + 0.032 | 83 | 44.39 |
| indoxacarb | 0.8 | 50 | |
| | | found* | calc.** |
| compound (I-1-2)/compound (I-1-8)*** + indoxacarb (1:25) inventive | 0.032 + 0.8 | 83 | 58.5 |
| triazophos | 4 | 0 | |
| | | found* | calc.** |
| compound (I-1-2)/compound (I-1-8)*** + triazophos (1:125) inventive | 0.032 + 4 | 67 | 17 |
| | | Kill rate in % after 6[d] | |
| compound (I-1-1)/compound (I-1-7)*** | 0.16 | 33 | |
| | 0.032 | 0 | |
| carbaryl | 4 | 0 | |
| | | found* | calc.** |
| compound (I-1-1)/compound (I-1-7)*** + carbaryl (1:125) inventive | 0.032 + 4 | 50 | 0 |
| fluensulfone | 2000 | 0 | |
| | | found* | calc.** |
| compound (I-1-1)/compound (I-1-7)*** + fluensulfone (1:12500) inventive | 0.16 + 2000 | 67 | 33 |
| flufenoxuron | 0.8 | 0 | |
| | | found* | calc.** |
| compound (I-1-1)/compound (I-1-7)*** + flufenoxuron (1:25) inventive | 0.032 + 0.8 | 100 | 0 |
| imicyafos | 45 | 0 | |
| | | found* | calc.** |
| compound (I-1-1)/compound (I-1-7)*** + imicyafos (1:281.25) inventive | 0.16 + 45 | 83 | 33 |
| L-cyhalothrin | 0.032 | 0 | |
| | | found* | calc.** |
| compound (I-1-1)/compound (I-1-7)*** + L-cyhalothrin (1:1) inventive | 0.032 + 0.032 | 83 | 0 |
| lufenuron | 0.8 | 17 | |
| | | found* | calc.** |
| compound (I-1-1)/compound (I-1-7)*** + lufenuron (1:25) inventive | 0.032 + 0.8 | 67 | 17 |
| novaluron | 0.8 | 67 | |
| | | found* | calc.** |
| compound (I-1-1)/compound (I-1-7)*** + novaluron (1:25) inventive | 0.032 + 0.8 | 83 | 67 |
| profenophos | 4 | 17 | |
| | | found* | calc.** |
| compound (I-1-1)/compound (I-1-7)*** + profenophos (1:125) inventive | 0.032 + 4 | 67 | 17 |
| chloranthraniliprole | 0.032 | 50 | |
| | | found* | calc.** |
| compound (I-1-1)/compound (I-1-7)*** + chloranthraniliprole (1:1) inventive | 0.032 + 0.032 | 100 | 50 |
| spinosad | 0.16 | 0 | |
| | | found* | calc.** |
| compound (I-1-1)/compound (I-1-7)*** + spinosad (1:5) inventive | 0.032 + 0.16 | 33 | 0 |
| tebufenozide | 0.16 | 0 | |
| | | found* | calc.** |
| compound (I-1-1)/compound (I-1-7)*** + tebufenozide (1:5) inventive | 0.032 + 0.16 | 33 | 0 |
| pyridalyl | 4 | 0 | |
| | | found* | calc.** |
| compound (I-1-1)/compound (I-1-7)*** + pyridalyl (1:25) inventive | 0.16 + 4 | 50 | 33 |
| methoxyfenozide | 0.8 | 0 | |
| | | found* | calc.** |
| compound (I-1-1)/compound (I-1-7)*** + methoxyfenozide (1:5) inventive | 0.16 + 0.8 | 67 | 33 |
| cyromazine | 4 | 0 | |
| | | found* | calc.** |
| compound (I-1-1)/compound (I-1-7)*** + cyromazine (1:25) inventive | 0.16 + 4 | 50 | 33 |
| cyflumetofen | 4 | 17 | |
| | | found* | calc.** |
| compound (I-1-1)/compound (I-1-7)*** + cyflumetofen (1:25) inventive | 0.16 + 4 | 50 | 33 |

*found = effect found

**calc. = effect calculated by Colby's formula

***In the tested mixtures of compound (I-1-1)/compound (I-1-7) or compound (I-1-2)/compound (I-1-8), the compounds (I-1-1) and (I-1-2) were each present to an extent of approx. 85% or approx. 84%, and the compounds (I-1-7) and (I-1-8) each to an extent of approx. 15%.

Example D

*Tetranychus* Test (OP-Resistant/Spray Treatment)

Solvent: 78 parts by weight of acetone
1.5 parts by weight of dimethylformamide
Emulsifier: 0.5 part by weight of alkylaryl polyglycol ether To produce an appropriate active ingredient formulation, 1 part by weight of active ingredient is mixed with the stated amounts of solvent and emulsifier, and the concentrate is diluted with emulsifier-containing water to the desired concentration.

Discs of bean leaves (*Phaseolus vulgaris*) infested by all stages of the two-spotted spider mite (*Tetranychus urticae*) are sprayed with an active ingredient formulation of the desired concentration.

After the desired period of time, the effect in % is determined 100% means that all of the spider mites have been killed; 0% means that none of the spider mites have been killed.

In this test, the following active ingredient combination according to the present application exhibited a synergistic enhancement in activity compared to the active ingredients applied individually:

TABLE D

*Tetranychus urticae* test

| Active ingredient | Concentration in g/ha | Kill rate in % after $2^d$ | |
|---|---|---|---|
| compound (I-1-2)/ compound (I-1-8)*** | 4 | 0 | |
| | 0.8 | 0 | |
| | 0.16 | 0 | |
| | 0.032 | 0 | |
| compound (I-1-1)/ compound (I-1-7)*** | 4 | 0 | |
| | 0.8 | 0 | |
| | 0.16 | 0 | |
| | 0.032 | 0 | |
| acrinathrin | 4 | 20 | |
| | 0.8 | 0 | |
| | | found* | calc.** |
| compound (I-1-2)/ compound (I-1-8)*** + acrinathrin (1:25) inventive | 0.16 + 4 | 70 | 20 |
| alpha-cypermethrin | 4 | 0 | |
| | | found* | calc.** |
| compound (I-1-2)/ compound (I-1-8)*** + alpha-cypermethrin (1:1) inventive | 4 + 4 | 80 | 0 |
| compound (I-1-1)/ compound (I-1-7)*** + alpha-cypermethrin (1:1) inventive | 4 + 4 | 70 | 0 |
| bifenthrin | 0.16 | 0 | |
| | | found* | calc.** |
| compound (I-1-2)/ compound (I-1-8)*** + bifenthrin (1:1) inventive | 0.16 + 0.16 | 70 | 0 |
| compound (I-1-1)/ compound (I-1-7)*** + bifenthrin (1:1) inventive | 0.16 + 0.16 | 40 | 0 |
| carbaryl | 500 | 10 | |
| | | found* | calc.** |
| compound (I-1-2)/ compound (I-1-8)*** + carbaryl (1:125) inventive | 4 + 500 | 50 | 10 |
| chlorfenapyr | 4 | 10 | |
| | | found* | calc.** |
| compound (I-1-2)/ compound (I-1-8)*** + chlorfenapyr (1:5) inventive | 0.8 + 4 | 70 | 10 |

TABLE D-continued

*Tetranychus urticae* test

| Active ingredient | Concentration in g/ha | | |
|---|---|---|---|
| compound (I-1-1)/ compound (I-1-7)*** + chlorfenapyr (1:5) inventive | 0.8 + 4 | 80 | 10 |
| diafenthiuron | 100 | 0 | |
| | | found* | calc.** |
| compound (I-1-2)/ compound (I-1-8)*** + diafenthiuron (1:125) inventive | 0.8 + 100 | 70 | 0 |
| emamectin benzoate | 0.032 | 0 | |
| | | found* | calc.** |
| compound (I-1-2)/ compound (I-1-8)*** + emamectin benzoate (5:1) inventive | 0.16 + 0.032 | 30 | 0 |
| fenamiphos | 20 | 0 | |
| | | found* | calc.** |
| compound (I-1-2)/ compound (I-1-8)*** + fenamiphos (1:25) inventive | 0.8 + 20 | 20 | 0 |
| fenpyroximate | 0.8 | 0 | |
| | | found* | calc.** |
| compound (I-1-2)/ compound (I-1-8)*** + fenpyroximate (1:25) inventive | 0.032 + 0.8 | 50 | 0 |
| compound (I-1-1)/ compound (I-1-7)*** + fenpyroximate (1:25) inventive | 0.032 + 0.8 | 80 | 0 |
| flubendiamide | 20 | 0 | |
| | | found* | calc.** |
| compound (I-1-1)/ compound (I-1-7)*** + flubendiamide (1:5) inventive | 4 + 20 | 30 | 0 |
| fluensulfone | 2000 | 0 | |
| | | found* | calc.** |
| compound (I-1-1)/ compound (I-1-7)*** + fluensulfone (1:500) inventive | 4 + 2000 | 30 | 0 |
| gamma-cyhalothrin | 0.8 | 0 | |
| | | found* | calc.** |
| compound (I-1-1)/ compound (I-1-7)*** + gamma-cyhalothrin (1:1) inventive | 0.8 + 0.8 | 30 | 0 |
| lufenuron | 100 | 0 | |
| | | found* | calc.** |
| compound (I-1-1)/ compound (I-1-7)*** + lufenuron (1:25) inventive | 4 + 100 | 20 | 0 |
| milbemectin | 0.032 | 50 | |
| | | found* | calc.** |
| compound (I-1-1)/ compound (I-1-7)*** + milbemectin (1:1) inventive | 0.032 + 0.032 | 80 | 0 |
| spinosad | 20 | 20 | |

TABLE D-continued

| *Tetranychus urticae* test | | | |
|---|---|---|---|
| Active ingredient | Concentration in g/ha | | |
| | | found* | calc.** |
| compound (I-1-2)/ compound (I-1-8)*** + spinosad (1:5) inventive | 4 + 20 | 60 | 20 |
| spirodiclofen | 100 | 0 | |
| | | found* | calc.** |
| compound (I-1-2)/ compound (I-1-8)*** + spirodiclofen (1:25) inventive | 4 + 100 | 70 | 0 |
| compound (I-1-1)/ compound (I-1-7)*** + spirodiclofen (1:25) inventive | 4 + 100 | 80 | 0 |
| spirotetramat | 4 | 0 | |
| | | found* | calc.** |
| compound (I-1-2)/ compound (I-1-8)*** + spirotetramat (1:5) inventive | 0.8 + 4 | 20 | 0 |
| tebufenpyrad | 0.16 | 0 | |
| | | found* | calc.** |
| compound (I-1-1)/ compound (I-1-7)*** + tebufenpyrad (1:5) inventive | 0.032 + 0.16 | 40 | 0 |
| thiodicarb | 100 | 0 | |
| | | found* | calc.** |
| compound (I-1-2)/ compound (I-1-8)*** + thiodicarb (1:25) inventive | 4 + 100 | 50 | 0 |
| compound (I-1-1)/ compound (I-1-7)*** + thiodicarb (1:25) inventive | 4 + 100 | 70 | 0 |
| 4-{[(6-CHLOROPYRID-3-YL)METHYL](2,2-DIFLUOROETHYL)AMINO} FURAN-2(5H)-ONE | 20 | 0 | |
| | | found* | calc.** |
| compound (I-1-1)/ compound(I-1-7)*** + 4-{[(6-CHLOROPYRID-3-YL)METHYL](2,2-DIFLUOROETHYL)AMINO} FURAN-2(5H)-ONE (1:5) inventive | 4 + 20 | 20 | 0 |
| | | Kill rate in % after $6^d$ | |
| compound (I-1-2)/ compound (I-1-8)*** | 4 | 0 | |
| | 0.8 | 0 | |
| | 0.16 | 0 | |
| | 0.032 | 0 | |
| compound (I-1-1)/ compound (I-1-7)*** | 4 | 10 | |
| | 0.8 | 10 | |
| | 0.16 | 0 | |
| | 0.032 | 0 | |
| acrinathrin | 0.8 | 40 | |

TABLE D-continued

| *Tetranychus urticae* test | | | |
|---|---|---|---|
| Active ingredient | Concentration in g/ha | | |
| | | found* | calc.** |
| compound (I-1-2)/compound (I-1-8)*** + acrinathrin (1:25) inventive | 0.032 + 0.8 | 70 | 40 |
| compound (I-1-1)/compound (I-1-7)*** + acrinathrin (1:25) inventive | 0.032 + 0.8 | 80 | 40 |
| abamectin | 0.032 | 80 | |
| | 0.0064 | 0 | |
| | | found* | calc.** |
| compound (I-1-2)/compound (I-1-8)*** + abamectin (5:1) inventive | 0.16 + 0.032 | 100 | 80 |
| compound (I-1-1)/compound (I-1-7)*** + abamectin (5:1) inventive | 0.032 + 0.0064 | 70 | 0 |
| cadusaphos | 20 | 0 | |
| | | found* | calc.** |
| compound (I-1-2)/compound (I-1-8)*** + cadusaphos (1:25) inventive | 0.8 + 20 | 40 | 0 |
| carbaryl | 500 | 20 | |
| | | found* | calc.** |
| compound (I-1-2)/compound (I-1-8)*** + carbaryl (1:125) inventive | 4 + 500 | 70 | 20 |
| chlorpyrifos | 100 | 0 | |
| | | found* | calc.** |
| compound (I-1-2)/compound (I-1-8)*** + chlorpyrifos (1:25) inventive | 4 + 100 | 30 | 0 |
| compound (I-1-1)/compound (I-1-7)*** + chlorpyrifos (1:25) inventive | 4 + 100 | 70 | 10 |
| diafenthiuron | 20 | 10 | |
| | | found* | calc.** |
| compound (I-1-2)/compound (I-1-8)*** + diafenthiuron (1:125) inventive | 0.16 + 20 | 30 | 10 |
| L-cyhalothrin | 4 | 20 | |
| | | found* | calc.** |
| compound (I-1-1)/compound (I-1-7)*** + L-cyhalothrin (1:1) inventive | 4 + 4 | 70 | 28 |
| spinetoram | 4 | 20 | |
| | | found* | calc.** |
| compound (I-1-2)/compound (I-1-8)*** + spinetoram (1:1) inventive | 4 + 4 | 80 | 20 |
| spiromesifen | 20 | 80 | |
| | 4 | 70 | |
| | | found* | calc.** |
| compound (I-1-2)/compound (I-1-8)*** + spiromesifen (1:5) inventive | 4 + 20 | 100 | 80 |
| compound (I-1-1)/compound (I-1-7)*** + spiromesifen(1:5) inventive | 0.8 + 4 | 90 | 73 |
| tebufenpyrad | 4 | 40 | |

TABLE D-continued

| Tetranychus urticae test | | | |
|---|---|---|---|
| Active ingredient | Concentration in g/ha | | |
| | | found* | calc.** |
| compound (I-1-2)/compound (I-1-8)*** + tebufenpyrad (1:1) inventive | 4 + 4 | 90 | 40 |
| compound (I-1-1)/compound (I-1-7)*** + tebufenpyrad (1:1) inventive | 4 + 4 | 80 | 46 |
| tefluthrin | 20 | 0 | |
| | | found* | calc.** |
| compound (I-1-2)/compound (I-1-8)*** + tefluthrin (1:5) inventive | 4 + 20 | 40 | 0 |

*found = effect found

**calc. = effect calculated by Colby's formula

***In the tested mixtures of compound (I-1-1)/compound (I-1-7) or compound (I-1-2)/compound (I-1-8), the compounds (I-1-1) and (I-1-2) were each present to an extent of approx. 85% or approx. 84%, and the compounds (I-1-7) and (I-1-8) each to an extent of approx. 15%.

The invention claimed is:

1. An active ingredient combination comprising a synergistically active combination of at least one compound (I-1) selected from the group consisting of (I-1-1)

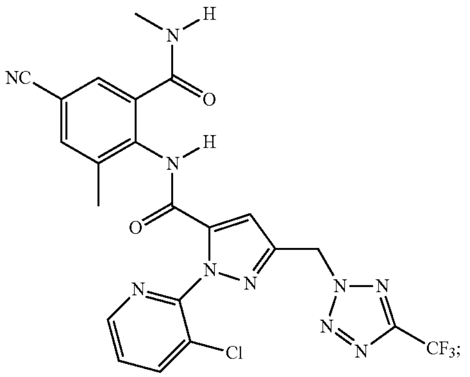

(I-1-2)

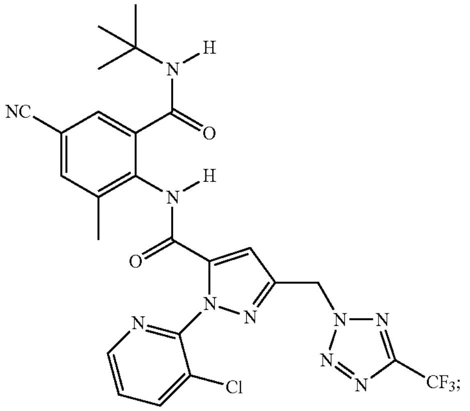

-continued (I-1-7)

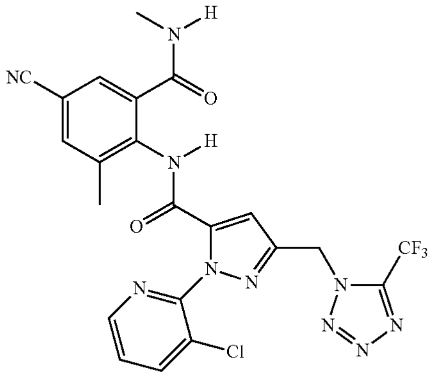

; and (I-1-8)

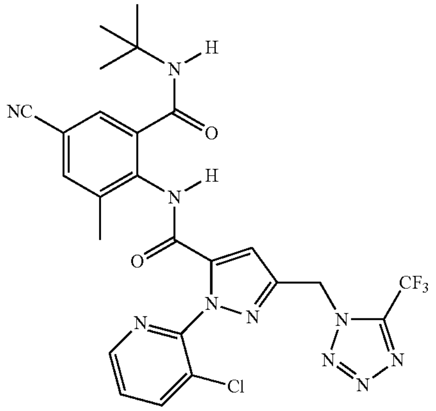

and one or more further insecticides and/or acaricides selected from group (II) consisting of
acrinathrin
alpha-cypermethrin
betacyfluthrin
cyhalothrin
cypermethrin
deltamethrin
lambda-cyhalothrin
gamma-cyhalothrin
transfluthrin
cyfluthrin
bifenthrin
tefluthrin
imidacloprid
acetamiprid
thiamethoxam
thiacloprid
dinotefuran
clothianidin
lufenuron
triflumuron
novaluron
flufenoxuron
buprofezin
methoxyfenozide
tebufenozide
fipronil
ethiprole
flubendiamide
chlorantraniliprole (Rynaxypyr)
cyazypyr
emamectin emamectin benzoate
abamectin
milbemectin
tebufenpyrad
fenpyroximate
diafenthiuron
spinosad
flonicamid
chlorfenapyr
metaflumizone
indoxacarb
chlorpyrifos
spirodiclofen
spiromesifen
spirotetramat
pyridalyl
spinetoram
acephate
triazophos
profenofos
fenamiphos
4-{[(6-chloropyrid-3-yl)methyl](2,2-difluoro-ethyl) amino}furan-2(5H)-one
cadusaphos
carbaryl
carbofuran
ethoprophos
thiodicarb
aldicarb
metamidophos
methiocarb
sulfoxaflor
*Bacillus firmus* 1-1582
dichloropropene
dimethoate
methomyl
imicyafos
fluensulfone and
11-(4-chloro-2,6-dimethylphenyl)-12-hydroxy-1,4-dioxa-9-azadispiro[4.2.4.2]tetradec-11-en-10-one and 2-{6-[2-(5-fluoropyridin-3-yl)-1,3-thiazol-5-yl]pyridin-2-yl}pyrimidine wherein the ratio of a compound or compounds of formula (I-1) to a compound or compounds of group (II) is 25:1 to 1:625, wherein the combination comprises a mixture of compounds selected from the group consisting of I-1-1/I-1-7, and I-1-2/I-1-8, and wherein the compound of the formula (I-1-1) to the compound of the formula (I-1-7) is present in a mixing ratio from 80:20 to 99:1, or wherein the compound of the formula (I-1-2) to the compound of the formula (I-1-8) is present in a mixing ratio from 80:20 to 99:1.

2. An agrochemical composition comprising an active ingredient combination according to claim 1, and at least one extender and/or surfactant.

3. A method for controlling animal pests, comprising allowing an active ingredient combination as defined in claim 1 to act on animal pests and/or their habitat.

4. A process for producing agrochemical compositions, comprising mixing an active ingredient combination as defined in claim 1 with at least one extender and/or surfactant.

5. An active ingredient combination according to claim 1, wherein the ratio of a compound or compounds of formula (I-1) to a compound or compounds of group (II) is 25:1 to 1:125.

6. An active ingredient combination according to claim 5 wherein the compounds of formula (I-1) comprise a mixture of compounds I-1-1 and I-1-7.

7. An active ingredient combination according to claim 5, wherein the compounds of formula (I-1) comprise a mixture of compounds I-1-2 and I-1-8.

8. An active ingredient combination according to claim 1, wherein the ratio of a compound or compounds of formula (I-1) to a compound or compounds of group (II) is 25:1 to 1:25.

9. An active ingredient combination according to claim 1, wherein the ratio of a compound or compounds of formula (I-1) to a compound or compounds of group (II) is 5:1 to 1:5.

10. An active compound combinations according to claim 1, comprising a mixture of compounds of the formula (I-1) of (I-1-1)/(I-1-7), where the compound of the formula (I-1-1) to the compound of the formula (I-1-7) is present in a mixing ratio from 80:20 to 99:1.

11. An active compound combinations according to claim 1, comprising a mixture of compounds of the formula (I-1) of (I-1-2)/(I-1-8), where the compound of the formula (I-1-2) to the compound of the formula (I-1-8) is present in a mixing ratio from 80:20 to 99:1.

12. An active ingredient combination according to claim 1, wherein the ratio of a compound or compounds of formula (I-1) to a compound or compounds of group (II) is 5:1 to 1:625.

* * * * *